United States Patent [19]

McCombs et al.

[11] Patent Number: 5,114,863
[45] Date of Patent: May 19, 1992

[54] IMMUNOSORBANT ASSAY FOR α-1-ANTITRYPSIN, KIT EMPLOYING SAID ASSAY, MONOCLONAL ANTIBODY TO α-1-ANTITRYPSIN, AND HYBRIDOMA FOR PRODUCING SAID MONOCLONAL ANTIBODY

[75] Inventors: Candace C. McCombs; Joseph P. Michalski, both of Covington; William R. Gallaher; James J. Thompson, both of New Orleans, all of La.

[73] Assignee: Board of Supervisors of Louisiana State University & Agricultural & Mechanical College, New Orleans, La.

[21] Appl. No.: 617,402

[22] Filed: Nov. 15, 1990

Related U.S. Application Data

[63] Continuation of Ser. No. 913,238, Sep. 30, 1986, abandoned.

[51] Int. Cl.$^5$ .................................. G01N 33/543
[52] U.S. Cl. ................... 436/518; 435/7.92; 435/70.21; 435/240.27; 435/970; 435/7.4; 436/528; 436/548; 436/805; 436/810; 530/388.25; 530/388.2; 530/389.3; 530/389.1
[58] Field of Search ............ 424/11, 101, 94.64; 435/7.9–7.95, 13, 174, 70.21, 240.27, 810, 188, 970, 975, 7.4; 436/513–514, 517–518, 536, 528, 543, 547–548, 805, 810, 823; 530/387, 808, 809

[56] References Cited

U.S. PATENT DOCUMENTS 4,590,157  5/1986  Chandler et al. ..................... 435/7

OTHER PUBLICATIONS

Michalski et al., "A Modified Double Antibody Sandwich Enzyme-Linked Immunosorbent Assay for Measurement of Alpha-1-Antitrypsin in Biologic Fluids", *J. Immun. Methods,* 83 (1985), 101–112.

Herion et al., Bioscience Reports, vol. 4, pp. 139–147 (1984) Great Britain.

Chandra et al., Biochemistry, vol. 22, No. 22, pp. 5055–5061 (Oct. 25, 1983).

(List continued on next page.)

*Primary Examiner*—Esther L. Kepplinger
*Assistant Examiner*—Carol A. Spiegel
*Attorney, Agent, or Firm*—Pravel, Gambrell, Hewitt, Kimball & Krieger

[57] ABSTRACT

A double antibody sandwich immunosorbent assay for detecting alpha-1-antitrypsin ($\alpha_1$AT) comprising the steps of: (1) reacting (a) a first-species-of-animal antibody to $\alpha_1$AT with (b) a solid substrate; (2) reacting (a) $\alpha_1$AT in a sample suspected of containing $\alpha_1$AT with (b) the first-species-of animal polyclonal antibody to $\alpha_1$AT; (3) reacting (a) a second-species-of-animal antibody to $\alpha_1$AT with (b) the $\alpha_1$AT in a sample suspected of containing $\alpha_1$AT; (4) reacting (a) a labelled antibody comprising a first-species-of-animal antibody to an antibody from a second species of animal with (b) the second-species-of-animal antibody to $\alpha_1$AT; and (5) detecting the amount of labelled first-species-of-animal antibody to antibody from the second species of animal that reacted with the second-species-of-animal polyclonal antibody to $\alpha_1$AT; provided that the first species of animal and the second species of animal are not the same in a given assay; and provided that steps (1) to (4) can be conducted in any order so as to result in a complex comprising: (i) the substrate complexed to (ii) the first-species-of-animal antibody to $\alpha_1$AT complexed to (iii) the $\alpha_1$AT complexed to (iv) the second-species-of-animal antibody to $\alpha_1$AT complexed to (v) the labelled antibody. The antibodies used in the assay can be polyclonal antibodies or monoclonal antibodies. A kit for detecting $\alpha_1$AT comprising reagents for conducting the above described assays. A monoclonal antibody having specific reactivity to $\alpha_1$AT, the antibody being further characterized in that it exhibits substantially no cross reactivity with albumin. A hybridoma that produces the above described monoclonal antibody.

13 Claims, 1 Drawing Sheet

OTHER PUBLICATIONS

Sveger, *Pediatric Research*, vol. 19, No. 8, pp. 834–835 (1985).

Travis et al., *Ann. Rev. Biochem.*, vol. 52, pp. 655–709 (1983).

Page 43 from the Copper Biomedical Catalog, listing the Cappel Monoclonal Antibodies to human alpha-1-antitrypsin. (Publication date not known-catalog states that prices are effective as of Mar. 1, 1985).

Michalski et al., "A Modified Double Antibody Sandwich Enzyme-Linked Immunosorbent Assay for Measurement of $\alpha$-1-Antitrypsin in Biologic Fluids", *J. Immun. Methods*, 83 (1985) 101–102.

Hallmark et al., "Monoclonal antibody specific for the mutant PiZ$\alpha_1$-antitrypsin and its application in an ELISA procedure for identification of PiZ gene carriers", PNAS 81 (1984), 5690–5693.

Kokai Tokkyo Koho, "Determination of $\alpha_1$-antitrypsin-trypsin complexes in human body fluids by the sandwich method (enzyme immunoassay)", *Chemical Abstracts* vol. 100, 1984, #2752d.

Herion et al., "Monoclonal antibodies against plasma protease inhibitors: II. Production and characterization of 25 monoclonal antibodies against human $\alpha_1$-antitrypsin Correlation between antigenic structure and functional sites", *Chem Abs* 100:155002j, 1984.

Collins, W. P. (ed.), *Alterative Immunoassay*, 1985 pp. 13, 14, 61 and 79–84.

Ehrlich et al., "Mixing Two Monoclonal Antibodies Enhanced Affinity for Antigen", *J. Immun.*, vol. 128, No. 6, pp. 2709–2713, Jun. 6, 1982.

Zola et al., "Techniques for the Production and Characterization of Monoclonal Hybridoma Antibodies", in *Monoclonal Hybridoma Antibodies: Techniques and Applications*, 1982, pp. 1, 19 and 23.

*Monoclonal Hybridoma Antibodies: Techniques and Applications*, 1982, pp. 1, 19 and 23.

IMMUNOSORBANT ASSAY FOR α-1-ANTITRYPSIN, KIT EMPLOYING SAID ASSAY, MONOCLONAL ANTIBODY TO α-1-ANTITRYPSIN, AND HYBRIDOMA FOR PRODUCING SAID MONOCLONAL ANTIBODY

"This is a continuation application of copending application Ser. No. 913,238 filed on Sep. 30, 1986 and now abandoned."

FIELD OF THE INVENTION

The present invention relates to an immunosorbent assay, specifically a double antibody sandwich immunosorbent assay for detecting alpha-1-antitrypsin (hereinafter "$\alpha_1$AT") in biological fluids including serum, synovial fluid, saliva and bronchoalveolar lavage fluids using a polyclonal antibody to $\alpha_1$AT or a monoclonal antibody to $\alpha_1$AT. The present invention also relates to a kit for detecting $\alpha_1$AT using the above assay. Additionally the present invention relates to a novel monoclonal antibody that specifically binds $\alpha_1$AT, but has substantially no cross reactivity with human albumin, and to a hybridoma cell line capable of producing the monoclonal antibody.

BACKGROUND OF THE INVENTION $\alpha_1$AT is a glycoprotein of approximately 53 kDA that functions as the major protease inhibitor in human serum. It is synthesized predominantly in the liver, although small quantities may also be produced locally, for example, by alveolar macrophages (White. R., D. Lee. G. G. Habicht and A. Janoff. 1981. *Am. Rev. Respir. Dis.* 123. 447). There has been much recent interest in the possible role of $\alpha_1$AT in the pathogenesis of many human diseases (reviewed in Lieberman. J.. 1980. in: *Current Pulmonology,* Vol. 2. ed. D. H. Simmond (Houghton. Mifflin Publishers. Boston, Mass.) pp. 41-68 and Fagerhol. M. K. and D. W. Cox. 1981. in: *Advances in Human Genetics,* Vol. 3. eds. H. Harris and K. Kirschhorn (Plenum Press. New York) pp. 1-62) because of its role in protecting tissues from damage resulting from local release of proteolytic enzymes and the demonstration that genetic variants of $\alpha_1$AT are associated with pulmonary and liver disease. Previously available methods for measuring $\alpha_1$AT in serum have proved less than satisfactory for measuring $\alpha_1$AT in other biologic fluids. For example, measurement by radial immunodiffusion (RID) frequently requires laborious concentration of fluids, with significant and unpredictable loss of $\alpha_1$AT (Warr. G. A., R. R. Martin, P. M. Sharp and R. D. Rossen. 1977, *Am. Rev. Respir. Dis.* 116, 25).

Methods previously used to quantitate $\alpha_1$AT include electroimmunodiffusion (Manildi. E. R., 1972. *Clin. Chem.* 18, 1019). nephelometry (Holzer, K. H. and G. Binzus, 1963. *Verh. Dtsch. Ges. Inn. Med.* 69. 456 and Gaidulis. L., H. A. Muensch, W. C. Maslow and W. Z. Borer, 1983, *Clin. Chem.* 29, 1838). and radial immunodiffusion (Mancini, G., A. O. Carbonara and J. F. Heremans. 1965, *Int. J. Immunochem.* 2, 235 and Dietz, A. A., H. M. Rubinstein and L. Hodges. 1974. *Clin. Chem.* 20, 396). All give comparable results in measuring serum $\alpha_1$AT. The simplicity of the RID method, and the commercial availability of RID kits for measuring $\alpha_1$AT, have made it the standard method of quantitating $\alpha_1$AT in serum. For the protective function of $\alpha_1$AT to be assessed, local concentrations should also be measured at sites of inflammation, protease release and tissue damage. For measuring $\alpha_1$AT in biologic fluids other than serum, the previously used methods have been less than satisfactory.

A number of investigators have measured $\alpha_1$AT in synovial fluids from patients with inflammatory diseases, where proteases are thought to play an important role in joint destruction (Swedlund H. A., G. G. Hunder and G. J. Gleich, 1974. *Ann. Rheum. Dis.* 33, 162: Brackertz, D., J. Hagmann and F. Kaepers. 1975, *Ann. Rheum. Dis.* 34. 225; Hadler, N. M., A. M. Johnson, J. K. Spitznagel and R. J. Quinet. 1981. *Ann. Rheum. Dis.* 40, 55: Ekerot. L. and K. Ohlsson. 1982. *Rheumatol. Int.* 2, 21: Pritchard. M. H., 1984. *Ann. Rheum. Dis.* 43, 50: and Virca, G. D., R. K. Mallya. M. Pepys and H. P. Schnebli, 1984. in: *Proteases: Potential Role in Health and Disease,* eds. W. H. Horl and A. Heidland (Plenum Press. New York)). Levels of $\alpha_1$AT in synovial fluids are roughly equivalent to serum levels, but investigators using different methods have obtained discrepant results. One reason appears to be that complexing of $\alpha_1$AT to proteases or to hyaluronic acid, both abundant in synovial fluid, impairs the migration of $\alpha_1$AT through gels, thus giving falsely low values (*Molecular Biology of Human Proteins with Special Reference to Plasma Proteins,* (Schultz. H. E. and J. F. Heremans eds., 1966. (Elsevier. New York)): Brackertz, D. J. Hagmann and F. Kaepers. 1975. *Ann. Rheum. Dis.* 34, 225; Ochi, T. K., K. Yonemasu and K. Ono, 1980. *Ann. Rheum. Dis.* 39. 235: Ekerot. L. and K. Ohlsson. 1982, *Rheumatol. Int.* 2. 21; and Cawston T. E., E. Mercer, M. DeSilva and B. L. Hazleman. 1984, *Arthritis Rheum.* 27, 285).

Measurement of $\alpha_1$AT in bronchoalveolar lavage fluids is of particular interest because of the association of $\alpha_1$AT deficiency with pulmonary disease. Several studies have attempted to measure $\alpha_1$AT in lavage fluids, and have found it necessary to concentrate the lavage fluid by membrane filtration before electroimmunodiffusion (Warr. G. A., R. R. Martin, P. M. Sharp and R. D. Rossen. 1977. *Am. Rev. Respir. Dis.* 116, 25.; Gadek, J. E., H. G. Klein, P. V. Holland and R. G. Crystal, 1981. *J. Clin. Invest.* 68. 1158) or RID quantitation (Olsen, G. N., J. O. Harris, J. R. Castle, R. H. Welchman and H. J. Karmgard, 1975, *J. Clin. Invest.* 55, 427: Niederman, M. S., L. L. Fritts, W. M. Merrill, R. B. Fick, R. A. Matthay, H. Y. Reynolds and J. B. L. Gee, 1984, *Am. Rev. Respir. Dis.* 129. 943). Concentrating lavage fluids resulted in the loss of 55%±10% of the $\alpha_1$AT from the solutions, decreasing the accuracy of the results (Warr, G. A., R. R. Martin, P. M. Sharp and R. D. Rossen, 1977. *Am. Rev. Respir. Dis.* 116. 25).

Measurement of $\alpha_1$AT in human saliva has only recently been successful. Grimound and associates, using laser nephelometry, found a mean concentration of 0.57±0.27 mg/dl of $\alpha_1$AT in saliva from 35 normal subjects (Grimound. A. M., D. Duffault, J. P. Lodter and J. P. Seguela, 1984, *J. Biol. Buccale* 12. 67). Two previous attempts to measure $\alpha_1$AT by electroimmunodiffusion found that levels measured were below the limits of detection by this technique (Ryley. H. C. and T. D. Brosan. 1973. *J. Clin. Pathol.* 26. 852; Gersel, A. V. and N. Pedersen, 1979, *Int. J. Oral Surg.* 8, 212).

So far as monoclonal antibodies to alpha-1-antitrypsin are concerned, only one is known. This is available from Cappel Laboratories (hereinafter referred to as the "Cappel antibody"). However, serious problems exist in use of the Cappel antibody in $\alpha_1$AT assays in that the Cappel antibody does not react strongly with $\alpha_1$AT and, even more importantly, the Cappel antibody cross reacts strongly with human albumin. The cross reaction with human albumin virtually eliminates the Cappel antibody as a candidate for a reagent to be used in any assay for $\alpha_1$AT employing body fluids.

SUMMARY OF THE INVENTION

Accordingly, one object of the present invention is to provide a double antibody sandwich immunosorbent assay that can be used to directly measure concentrations of $\alpha_1$AT in fluids, particularly the low concentrations in fluids such as saliva and bronchoalveolar lavage fluids as well as the higher concentrations present in fluids such as serum and synovial fluid.

Another object of the invention is to provide a test kit for measurement and/or screening for $\alpha_1$AT using the above-described assay.

A further object of the invention is to provide a monoclonal antibody that specifically binds to $\alpha_1$AT but exhibits substantially no cross reactivity with human albumin.

An even further object of the invention is to provide a hybridoma capable of producing the above-described monoclonal antibody.

These and other objects are obtained by providing a double antibody sandwich immunosorbent assay for detecting $\alpha_1$AT comprising the steps of:

(1) reacting
(a) a first-species-of-animal polyclonal antibody to $\alpha_1$AT with
(b) a solid substrate:
(2) reacting
(a) $\alpha_1$AT in a sample suspected of containing $\alpha_1$AT with
(b) said first-species-of-animal polyclonal antibody to $\alpha_1$AT;
(3) reacting
(a) a second-species-of-animal polyclonal antibody to $\alpha_1$AT with
(b) said $\alpha_1$AT in a sample suspected of containing $\alpha_1$AT;
(4) reacting
(a) a labelled antibody comprising a first-species-of-animal antibody to an antibody from a second species of animal with
(b) said second-species-of-animal polyclonal antibody to $\alpha_1$AT; and
(5) detecting the amount of said labelled first-species-of-animal antibody to antibody from said second species of animal that reacted with said second-species-of-animal polyclonal antibody to $\alpha_1$AT;

provided that said first species of animal and said second species of animal are not the same in a given assay; and provided that said steps (1) to (4) can be conducted in any order so as to result in a complex comprising: (i) said substrate complexed to (ii) said first-species-of-animal antibody to $\alpha_1$AT complexed to (iii) said $\alpha_1$AT complexed to (iv) said second-species-of-animal antibody to $\alpha_1$AT complexed to (v) said labelled antibody.

The present invention also provides a double antibody sandwich immunosorbent assay for detecting $\alpha_1$AT comprising the steps of:

(1) reacting
(a) a first-species-of-animal polyclonal antibody to $\alpha_1$AT with
(b) a solid substrate;
(2) reacting
(a) $\alpha_1$AT in a sample suspected of containing $\alpha_1$AT with
(b) said first-species-of-animal polyclonal antibody to $\alpha_1$AT;
(3) reacting
(a) a labelled second-species-of-animal polyclonal antibody to $\alpha_1$AT with
(b) said $\alpha_1$AT in a sample suspected of containing $\alpha_1$AT; and
(4') detecting the amount of said labelled second-species-of-animal polyclonal antibody that reacted with said $\alpha_1$AT:

provided that said first species of animal and said second species of animal can be the same in a given assay: and provided that said steps (1) to (3) can be conducted in any order so as to result in a complex comprising: (i) said substrate complexed to (ii) said first-species-of-animal antibody to $\alpha_1$AT complexed to (iii) said $\alpha_1$AT complexed to (iv) said labelled second-species-of-animal antibody to $\alpha_1$AT.

Further, according to the present invention, any of the antibodies in either of the two above described assays, with certain provisos, can be monoclonal antibodies. The monoclonal antibodies which are particularly useful in the two above-described assays are monoclonal antibodies to $\alpha_1$AT which are further characterized in that substantially no cross reactivity with albumin from a source of the $\alpha_1$AT exists.

According to the present invention there is also provided a double antibody sandwich immunosorbent assay kit for detecting $\alpha_1$AT comprising:

(1) a first-species-of-animal antibody to $\alpha_1$AT;
(2) a second-species-of-animal antibody to $\alpha_1$AT;
(3) a labelled antibody comprising a first-species-of-animal antibody to antibody from the second species of animal;
(4) optionally, means for detecting the labelled first-species-of-animal antibody; and
(5) optionally, a substrate for said first-species-of-animal antibody to $\alpha_1$AT;

provided that the first species of animal and second species of animal are not the same for a given assay.

In another embodiment, the present invention provides a double antibody sandwich immunosorbent assay kit for detecting $\alpha_1$AT comprising:

(1) a first-species-of-animal antibody to $\alpha_1$AT;
(2) a labelled second-species-of-animal antibody to $\alpha_1$AT;
(3) optionally, means for detecting said labelled antibody; and
(4) optionally, a substrate for said first-species-of-animal antibody to $\alpha_1$AT;

provided that the first species of animal and the second species of animal can be the same in a given assay.

Still further, the present invention also provides a monoclonal antibody having specific reactivity to $\alpha_1$AT, the antibody being further characterized in that it exhibits substantially no cross reactivity with albumin from a source of the $\alpha_1$AT.

Even further, the present invention provides a hybrid continuous cell line (hybridoma) that produces monoclonal antibody to $\alpha_1$AT, the antibody being further characterized in that it exhibits substantially no cross reactivity with albumin from a source of the $\alpha_1$AT, which comprises a cell hybrid of an animal spleen cell immunized with $\alpha_1$AT fused to a myeloma cell derived from the same animal species as the spleen cell.

Even further, the present invention provides a composition comprising:

(1) a hybrid continuous cell line (hybridoma) that produces monoclonal antibody to $\alpha_1$AT, the antibody being further characterized in that it exhibits substantially no cross reactivity with albumin from a source of the $\alpha_1$AT, which comprises a cell hybrid of an animal spleen cell immunized with $\alpha_1$AT fused to a myeloma cell derived from the same animal species as the spleen cell; and (2) a culture medium for the hybridoma.

DETAILED DESCRIPTION OF THE INVENTION

Figure 1:
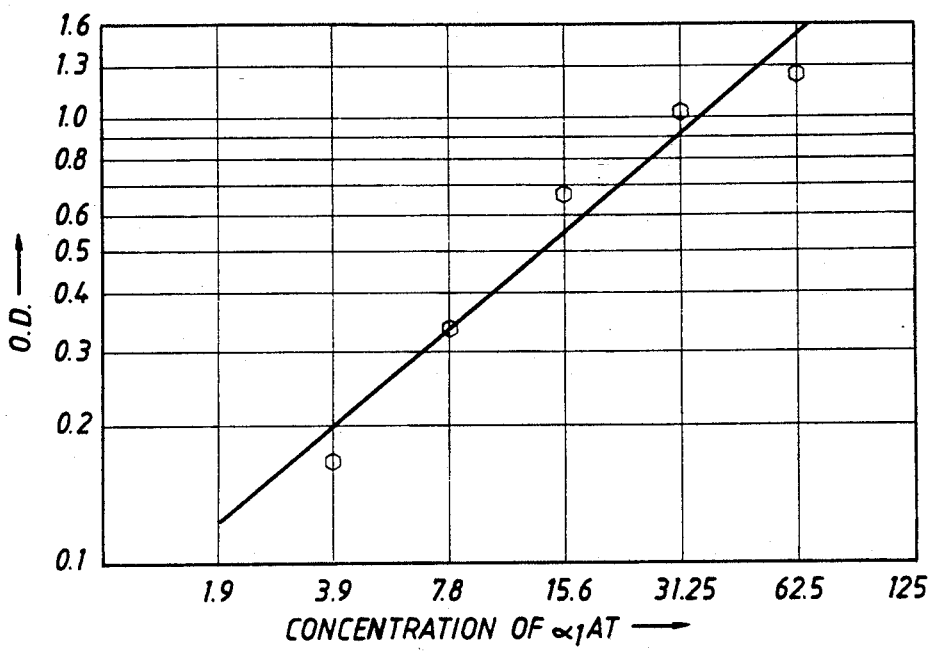
FIG. 1 is a standard curve for alpha-1-antitrypsin measured by an enzyme-linked immunosorbent assay ("ELISA") of this invention using polyclonal antibodies plotted on a log/log scale. Abscissa: 2-fold dilution of serum expressed as ng/ml of $\alpha_1$AT; ordinate: optical density at 410 nm=, coefficient of correlation (F) 0.98 by regression analysis.

The immunosorbent assay method embodiment of this invention gives results comparable to other methods in measuring $\alpha_1$AT in serum, but is much more useful than prior methods for measuring $\alpha_1$AT in biologic fluids other than serum. The double antibody sandwich assay can accurately quantitate $\alpha_1$AT at concentrations as low as 15-20 ng/ml. This sensitivity makes it especially useful for measuring $\alpha_1$AT in materials with very low concentrations of $\alpha_1$AT, such as bronchoalveolar lavage fluids or saliva. Concentration of solutions, with variable loss of $\alpha_1$AT on the filter membranes, has been necessary in most previous investigations.

A second advantage of the present immunosorbent assay is that it is not considered subject to interference by factors that interfere with the diffusion of $\alpha_1$AT through gels. This is especially relevant to synovial fluid, where the high concentration of hyaluronic acid and the binding of $\alpha_1$AT to proteases have been identified as factors leading to the underestimation of $\alpha_1$AT by the RID and electrodiffusion methods (Schultz. H. E. and J. F. Heremans (eds.). 1966. *Molecular Biology of Human Proteins with Special Reference to Plasma Proteins* (Elsevier, N.Y.); Brackertz. D., J. Hagmann and F. Kaepers, 1975, *Ann. Rheum. Dis.* 34. 225; Ochi, T. K., K. Yonemasu and K. Ono, 1980. *Ann. Rheum. Dis.* 39. 235: Ekerot. L. and K. Ohlsson, 1982, *Rheumatol. Int.* 2. 21; Cawston, T. E., E. Meroer, M. DeSilva and B. L. Hazleman. 1984, *Arthritis Rheum.* 27, 285).

Double Antibody Sandwich Immunosorbent Assay Using Polyclonal Antibody To $\alpha_1$AT According to this embodiment of the invention, it is preferred that the steps described below be conducted in the numerical order given. However, it is to be understood that: (A) steps (1) to (4) in the assay employing an unlabelled antibody in step (3) can be conducted in any order so as to result in a complex comprising: (i) a substrate complexed to (ii) a first-species-of-animal antibody to $\alpha_1$AT complexed to (iii) $\alpha_1$AT complexed to (iv) a second-species-of-animal antibody to $\alpha_1$AT complexed to (v) a labelled first-species-of-animal antibody to an antibody from a second species of animal and (B) steps (1) to (3) in the assay employing a labelled antibody in step (3) can be conducted in any order so as to result in a complex comprising:. (i) a substrate complexed to (ii) a first-species-of-animal antibody to $\alpha_1$AT complexed to (iii) $\alpha_1$AT complexed to (iv) a labelled second-species-of-animal antibody to $\alpha_1$AT. Further, it is understood that reference to an antibody or antigen includes the appropriate complexed antibodies or antigens that would be present in accordance with the order in which the steps are being conducted.

Exemplification of this embodiment of this invention is given below as to the steps thereof conducted in the order listed, but this is merely for convenience and illustration only.

The first step, step (1). of this embodiment of the assay comprises reacting a first-species-of-animal polyclonal antibody to $\alpha_1$AT with a solid substrate.

Suitable substrates are known to those skilled in the art and include polystyrene or polyvinyl wells, microporous filters, nitrocellulose or nylon membranes. magnetic particles, and polymeric tubes, cuvettes, beads and discs. The preferred solid substrate is polyvinyl chloride, preferably in the form of flat-bottomed plates.

The reaction is carried out by diluting the polyclonal antibody in a suitable buffer such as carbonate/bicarbonate buffer (Dalory G. E. and E. J. King, 1945, *Biochem. J.* 39. 245). to a suitable concentration and then adding an appropriate amount of antibody to microplate wells or other solid substrates, followed by incubation at a suitable temperature in a humidified chamber such that the first-species-of-animal antibody adheres to the surface of the substrate.

Buffers, other than carbonate/bicarbonate buffers, which can be used in the present invention include any buffer which solubilizes immunoglobulin without denaturing it. Numerous such buffers are known to those skilled in the art, for example, phosphate buffered saline.

The final concentration of the polyclonal antibody on dilution should be in the range of 100 ng/ml to 100 $\mu$g/ml. The most preferred concentration is about 25 $\mu$g/ml.

The volume of antibody solution added to each well or other solid substrate depends upon the surface area of the bottom of the well or the surface area of the other solid substrate. For example, if the antibody is at a concentration of 25 $\mu$g/$\mu$l, and the bottom of the microplate wells are 0.283 cm$^2$, about 100 $\mu$l of antibody solution would be added to the well.

Incubation is carried out for a sufficient time and at a temperature such that the antibody adheres to the surface of the substrate. Suitable incubation times and temperatures can readily be determined by those skilled in the art. For the present invention, generally a suitable incubation time and temperature is overnight (about 18 hours) at 4° C.

The humidified chamber should have a relative humidity of close to 100%, although this can be varied to some extent.

After incubation, the wells or other solid substrates are rinsed with a suitable reagent such a PBS-TWEEN (TWEEN is a tradename for an emulsifying agent comprising a complex mixture of polyoxyethylene derivatives of fatty acid partial esters of hexitol anhydrides), or other buffer containing blocking agents. The buffer can be any which solubilizes the $\alpha_1AT$ to be assayed without denaturing it, and the blocking agent can be gelatin, milk proteins, or detergents such as PBS-TWEEN, TRITON X (TRITON is a tradename for a surfactant based on alkylaryl polyether alcohols, sulfonates and sulfates, produced by Rohm and Haas Co.). NP 40 (produced by Shell Chemical Co.) or SDS. The preferred blocking buffer is PBS-TWEEN, which consists of phosphate buffered saline at pH 7.4 plus 0.05% TWEEN 20 (Manual Of Clinical Immunology (ed. by Noel R. Rose and Herman Friedman.) Am. Soc. for Microbiol., Wash. D.C., 1980).

The second step, step (2). of the assay comprises reacting $\alpha_1AT$ in a sample suspected of containing $\alpha_1AT$ with a first-species-of-animal polyclonal antibody to $\alpha_1AT$.

The sample used in the second step of the assay is diluted in a suitable buffer such that the final concentration is expected to be between 5 and 250 ng/ml.

Because of the wide variation in the concentration of $\alpha_1AT$ in various biological fluids it is useful to first identify the approximate range of $\alpha_1AT$ in the sample by assaying consecutive 10-fold dilutions and then more precisely quantitate the concentration of $\alpha_1AT$ with an assay using appropriately chosen 2-fold dilutions.

Suitable buffers for diluting the sample are readily known to those skilled in the art and include reagents such as PBS-TWEEN, or other blocking buffers as used in step (1).

If the first-species-of-animal antibody to $\alpha_1AT$ is already adhered to a substrate, the volume of sample containing $\alpha_1AT$ added to the first-species-of-animal antibody to $\alpha_1AT$ generally is a volume sufficient to coat the reacted surface of the well or other solid substrate.

If the reaction is being conducted in solution, without one of the reactants comprising a solid substrate, then the reactants are combined in a suitable blocking buffer, such as those described above. In this embodiment, the volume of reaction solution and the concentration of reactants is not critical, and can readily be determined by those skilled in the art.

The reaction between the polyclonal antibody to $\alpha_1AT$ and the $\alpha_1AT$ in the sample suspected of containing $\alpha_1AT$ is then carried out for a time and at a temperature sufficient to cause the $\alpha_1AT$ to complex with the antibody.

Suitable incubation times and temperatures are readily determined by those skilled in the art. According to the present invention, in general a suitable incubation time ranges from 5 minutes to 18 hours, and a suitable incubation temperature ranges from 4° C. to 37° C. A preferred incubation time and temperature is 2 hours at 37° C.

After completion of this incubation, the complex is purified.

If the first-species-of-animal antibody to $\alpha_1AT$ is already adhered to a solid substrate, then the purification is accomplished by rinsing the wells or other solid substrate as above, with a suitable buffer such as PBS-TWEEN, or other blocking buffer as described above.

If the first-species-of-animal antibody to $\alpha_1AT$ is not yet adhered to a solid substrate then the complex is purified by methods known to those skilled in the art, including membrane filtration, precipitation, or adsorption on an antibody coated substrate. For further reaction in solution the complex is resuspended in a suitable blocking buffer such as those described above. In this embodiment, the concentration of the complex in solution is not critical, and suitable concentrations are readily determined by the skilled artisan.

In a preferred embodiment of the present invention relevant to step (2). referred to herein as the "paddle embodiment", wherein the reaction steps are conducted out of order and wherein the first-species-of-animal antibody to $\alpha_1AT$ is already adhered to a substrate, the $\alpha_1AT$ which is to be reacted with the first-species-of-animal antibody to $\alpha_1AT$ has already been reacted with a labelled antibody. This embodiment is particularly useful for test kits wherein the sample suspected of containing $\alpha_1AT$ is reacted with the labelled antibody, and then a solid substrate, such as a paddle, having first-species-of-animal antibody adhered thereto, is dipped into the reaction mixture containing $\alpha_1AT$ complexed to labelled antibody and the $\alpha_1AT$ complex then complexes to the antibody on the solid substrate to give the final labelled product for diagnosis.

The third reaction step, step (3). of the assay involves reacting a second-species-of-animal polyclonal antibody to $\alpha_1AT$ with the $\alpha_1AT$ in a sample suspected of containing $\alpha_1AT$.

In order to conduct the third reaction step of the assay, the second-species-of-animal polyclonal antibody to $\alpha_1AT$ is diluted in a suitable reagent to a concentration determined empirically from titration curves (dilution vs. OD) and may range from 1.5 µg/ml to 30. µg/ml and may comprise a dilution of antiserum of from 1:2000 to 1:100.

If the $\alpha_1AT$ has already been reacted such that it is in a complex adhered to a solid substrate, the 1 second-species-of-animal polyclonal antibody to $\alpha_1AT$ is added to the well or other solid substrate in a suitable buffer, such as the blocking buffers described above and generally in the same volume as was used for the first-species-of-animal antibody and $\alpha_1AT$ sample.

If the reaction is being conducted in solution, without one of the reactants comprising a solid substrate, then the reactants are combined in a suitable blocking buffer, such as those described above. In this embodiment, the volume of reaction solution and the concentration of reactants is not critical, and can readily be determined by those skilled in the art.

Incubation is then conducted for a time and at a temperature sufficient to form a complex between the $\alpha_1AT$ and the second-species-of-animal polyclonal antibody to $\alpha_1AT$.

A suitable incubation time and temperature can also be readily determined by those skilled in the art. For example, a suitable incubation time ranges from 5 minutes to overnight, and a suitable incubation temperature ranges from 4° C. to 37° C. A preferred incubation time and temperature is 2 hours at 37° C.

As with the above reaction, this reaction is also conducted in a humidified chamber, under the conditions as described above for step (1).

After completion of this incubation, the complex is purified.

If the $\alpha_1$AT is in a complex already adhered to a solid substrate, then purification is accomplished by rinsing the wells or other solid substrate as above, with a suitable buffer such as PBS TWEEN, or other blocking buffer as used in step (2).

If the $\alpha_1$AT is not yet in a complex adhered to as solid substrate, then the complex including the second-species-of-animal polyclonal antibody to $\alpha_1$AT is purified by methods known to those skilled in the art, as described above (e.g. membrane filtration, precipitation, etc.). For further reaction in solution, the complex is resuspended in a suitable blocking buffer such as those described above. Further, as described above, the concentration of the complex in solution is not critical, and suitable concentrations are readily determined by the skilled artisan.

The polyclonal antibody used in the third step may be unlabelled, or may be labelled, as described in more detail below.

If the antibody used in the third step of the assay is labelled, the fourth step, designated "(4')" of the assay comprises detecting the amount of labelled second-species-of-animal polyclonal antibody in the final complex adhered to the substrate, as described in more detail below.

If the antibody used in the third step of the assay is unlabelled, the fourth step, designated "(4)". of the assay comprises reacting a labelled antibody which is derived from the same species of animal as the antibody used in the first step of the reaction and which is specific to any antibody from the second animal species from which the second-species-of-animal polyclonal antibody was derived with a second-species-of-animal polyclonal antibody to $\alpha_1$AT such that the two antibodies become complexed. An antibody from a third species of animal could be used for the second-species-of-animal polyclonal antibody in this step, but use of an antibody from the first species of animal is strongly preferred due to possible contamination of antibody from a third species of animal with antibody specific to antibody from the first species of animal.

In order to conduct this fourth reaction step of the assay, wherein the antibody used in the third step is unlabelled, the labelled first-species-of-animal antibody is diluted in a suitable reagent to a concentration determined empirically from titration curves (dilution vs. OD) and may range from 100 ng/ml to 500 μg/ml, and may comprise a dilution of antiserum of from 1:10,000 to 1:100.

If the second-species-of-animal antibody has already been reacted such that it is in a complex adhered to a solid substrate, the labelled first-species-of-animal antibody is added to the well or other solid substrate in a suitable buffer, such as the blocking buffers described above, and generally in the same volume as was used for the first-species-of-animal antibody $\alpha_1$AT sample.

If the reaction is being conducted in solution, without one of the reactants comprising a solid substrate, then the reactants are combined in a suitable blocking buffer, such as those described above. In this embodiment, the volume of reaction solution and the concentration of reactants is not critical, and can readily be determined by those skilled in the art.

Incubation is then conducted for a suitable amount of time and at a suitable temperature necessary to form a complex between the second-species-of-animal antibody and the labelled first-species-of-animal antibody.

Suitable incubation times range from 5 minutes to overnight and suitable incubation temperatures include 4° C. to 37° C.

In the present invention, it is preferred that the incubation take place for 2 hours at room temperature (about 25° C.).

After completion of this incubation, the complex is purified.

If the labelled first-species-of-animal antibody is already adhered to a solid substrate, then purification is accomplished by washing the wells or other solid substrate with a suitable reagent such as PBS-TWEEN, or other blocking buffer as used in steps (2) and (3).

If the labelled first-species-of-animal antibody is not yet in a complex adhered to a solid substrate, then the complex is purified by methods known to those skilled in the art, as described above e.g. membrane filtration, precipitation, etc.). For further reaction in solution, the complex is resuspended in a suitable blocking buffer such as those described above. Further, as described above, the concentration of the complex in solution is not critical and suitable concentrations are readily determined by the skilled artisan.

According to the final step of the assay, the amount of complexed labelled antibody is detected by a method suitable for the type of label used. This is step (4') of the assay using a labelled second-type-of-animal polyclonal antibody to $\alpha_1$AT and step (5) of the assay using a labelled antibody comprising a first-species-of-animal antibody to an antibody from a second species of animal.

According to the assay using only polyclonal antibody to $\alpha_1$AT, the $\alpha_1$AT for developing the polyclonal antibody may be from any mammalian source. Suitable mammalian sources include humans, rats, rabbits, or any other animals having an equivalent serine protease inhibitor. However, a preferred source is human-$\alpha_1$AT.

Of course, both the first-species-of-animal polyclonal antibody to $\alpha_1$AT used in the first reaction step of the assay and the second-species-of-animal polyclonal antibody to $\alpha_1$AT used in the second reaction step of the assay are antibodies to the particular $\alpha_1$AT to be assayed. Thus, for example, if the $\alpha_1$AT is human-$\alpha_1$AT, then the antibodies are antibodies to human-$\alpha_1$AT.

Further in accordance with the assay using only polyclonal antibody to $\alpha_1$AT, the first species of animal from which antibody is isolated can be any warm blooded animal including goats'sheep, rabbits, mice, or equines, etc. A preferred first species of animal is a goat.

If the assay is the assay wherein the second-species-of-animal antibody in step (3) is unlabelled, then the second species of animal can be any animal other than the first species of animal used to produce the first-species-of-animal antibody including mice. rabbits, or any other warm blooded animal. Goats can be used if the first-species-of-animal is not a goat.

If the assay is the assay wherein the second-species-of-animal antibody in step (3) is labelled, then the second species of animal can be the same as the first species of animal or different from the first species of animal.

According to the present invention preferred second species of animals include mice and rabbits, and rabbits are particularly preferred.

Isolation of antibodies to $\alpha_1AT$ from a first species of animal and antibodies to $\alpha_1AT$ from a second species of animal can be carried out according to methods known in the art. Whole antiserum can be used for the second-species-of-animal antibody, although affinity purified antibody is preferable. Affinity purified antibody is required for the first-species-of-animal antibodies used in steps (1) and (2) as well as step (4) of the embodiment using labelled antibody comprising a first-species-of-animal antibody to an antibody from a second species of animal. Affinity purification can be performed by numerous methods known to those skilled in the art (Ax'en R., J. Porath, and S. Ernback. 1967, *Nature* 214. 1302: Cuatrecasas P. and C. B. Anfinsen, 1971. *Annv. Rev. Biochem.* 40, 259.)

The labelled antibody according to the present invention is produced by complexing a labelling means to the antibody.

The labelling means or label used to label the antibody can be one of numerous labels known to those skilled in the art, including enzyme labels (such as peroxidase, e.g., horseradish peroxidase, alkaline phosphatase, or beta-gatactosidase). radioactive substance labels (such as $^{125}I$). fluorescent substance labels (such as fluorescein, rhodamine, or phycobiliproteins), enzyme, linking substances (such as biotin, avidin, streptavidin), etc.

According to the present invention, a preferred label is an enzyme label, and a preferred enzyme label is peroxidase, especially horseradish peroxidase.

Methods of conjugating the label to the antibody are well known to those skilled in the art. Techniques for antibody labelling are disclosed in: *Practical Immunoassay: The State of the Art*, edited by Wilfred R. Butt, Marcel Dekker, Inc.. New York. 1984. and these can be used in the present invention.

A particularly preferred labelled first-species-of-animal antibody to antibody from a second species of animal for use in the assay using only polyclonal antibodies to $\alpha_1AT$ is horseradish peroxidase-conjugated goat anti-rabbit IgG or horseradish peroxidase-conjugated goat anti-mouse IgG and particularly preferred is horseradish peroxidase-conjugated goat anti-rabbit IgG. The conjugation can be by, for example, the Nakane method (Nakane, P. K. and A. J. Kawaoi, 1974, *Histochem. Cytochem.* 22, 1084).

Detection of the amount of labelled antibody depends upon the type of label, and detection methods are well known to those skilled in the art as disclosed in: *Practical Immunoassav: The State of the Art*, edited by Wilfred R. Butt. Marcel Dekker Inc., New York. 1984.

When the label is peroxidase, a preferred method of detecting the amount of labelled antibody is by using a substrate solution comprising 2,-azino-di-(3-ethylbenzthiazolene sulfonic acid) (ABTS) and $H_2O_2$ in accordance with methods known in the art as disclosed in Makinem K. K. et al., 1982, *Analytical Biochem.* 126, 100. The amount of substrate acted upon by the peroxidase can then be determined by reading the optical densities of the reaction solutions using known techniques.

According to the present invention, concentrations of human-$\alpha_1AT$ as low as about 20 ng/ml can be measured.

The samples which can be analyzed in the present assay employing only polyclonal antibody to $\alpha_1AT$ include fluids such as blood serum, synovial fluid, saliva, bronchoalveolar lavage fluids, urine, stool, sputum, tears, semen, milk, peritoneal lavage fluid, amniotic fluid, cell culture supernatents or cell or tissue lysates. All should be diluted according to the guidelines given earlier. Blood serum, synovial fluid, saliva and bronchoalveolar lavage fluids are especially preferred.

Double Antibody Sandwich Immunosorbent Assay
Using At Least One Monoclonal Antibody This embodiment of the invention uses a monoclonal antibody as at least one of the antibodies in the assay. An embodiment which uses a monoclonal antibody as at least one of the antibodies to $\alpha_1AT$, is a particularly preferred embodiment.

As with the embodiment using only polyclonal antibodies to $\alpha_1AT$, it is preferred that the steps described below be conducted in numerical order. However, it is understood that: (A) steps (1) to (4) in the assay employing an unlabelled antibody in step (3) can be conducted in any order so as to result in a complex comprising: (i) a substrate complexed to (ii) a first-species-of-animal antibody complexed to (iii) $\alpha_1AT$ complexed to (iv) a second-species-of-animal antibody to $\alpha_1AT$ complexed to (v) a labelled first-species-of-animal antibody to an antibody from a second species of animal; and (B) steps (1) to (3) in the assay employing a labelled antibody in step (3) can be conducted in any order so as to result in a complex comprising: (i) a substrate complexed to (ii) a first-species-of-animal antibody to $\alpha_1AT$ complexed to (iii) $\alpha_1AT$ complexed to (iv) a labelled second-species-of-animal antibody to $\alpha_1AT$. Further it is understood that reference to an antibody or antigen includes the appropriate complexed antibodies or antigens that would be present in accordance with the order in which the steps are being conducted.

The steps below are described again in the order listed, but this is merely for convenience and illustration.

The first step, step (1). of this embodiment of the assay comprises reacting a first-species-of-animal antibody to $\alpha_1AT$ with a solid substrate.

Suitable substrates include those mentioned above for the assay using only polyclonal antibodies.

The reaction is carried out by diluting the antibody in a suitable coating buffer such as carbonate/bicarbonate buffer, to a suitable concentration and then adding an appropriate amount of antibody to microplate wells, or other solid substrates, followed by incubation at a suitable temperature in a humidified chamber as described above for the assay using only polyclonal antibodies.

Buffers, other than carbonate/bicarbonate buffers which can be used in this embodiment of the present invention include those mentioned above for the assay using only polyclonal antibodies.

The final concentration of the antibody on dilution should be in the range of 100 ng/ml to 100 µg/ml. The most preferred concentration is about 25 µg/ml.

The amount of antibody solution added to each well or other solid substrate depends upon the surface area of the bottom of the well or the surface area of the solid substrate and is an amount sufficient to coat the desired surface area. For example, if the antibody is at a concentration of 25 µg/ml, and the bottom of the microplate wells are 0.283 cm², generally about 100 µl of antibody solution would be added to the well or other solid substrate.

Incubation is carried out for a sufficient time and at a temperature such that the antibody adheres to the surface of the substrate. Suitable incubation times and temperatures can readily be determined by those skilled in the art. According to the present invention, a suitable incubation time and temperature is overnight (about 18 hours) at 4° C.

The humidified chamber should have a relative humidity of close to 100%, although some variation is permitted.

After incubation, the wells or other solid substrates are rinsed with a suitable reagent as described above for the assay using only polyclonal antibodies.

The second step, step (2), of the assay comprises reacting $\alpha_1AT$ in a sample suspected of containing $\alpha_1AT$ with a first-species-of-animal antibody to $\alpha_1AT$.

The samples used in the second step of the assay are diluted in a suitable buffer such that the final concentration is expected to be between 5 and 250 ng/ml.

As mentioned above, because of the wide variation in the concentration of $\alpha_1AT$ in various biological fluids it is useful to first identify the approximate range of $\alpha_1AT$ in the sample by assaying consecutive 10-fold dilutions and then more precisely quantitate the $\alpha_1AT$ concentration with an assay using appropriately chosen 2-fold dilutions.

Suitable buffers for diluting the samples are readily known to those skilled in the art and include reagents such as PBS-TWEEN, or other blocking buffers as used in step (1).

If the first-species-of-animal antibody to $\alpha_1AT$ is already adhered to a substrate, the volume of sample containing $\alpha_1AT$ added to the first-species-of-animal antibody to $\alpha_1AT$ generally is a volume sufficient to coat the reacted surface of the well or other solid substrate.

If the reaction is being conducted in solution, without one of the reactants comprising a solid substrate, then the reactants are combined in a suitable blocking buffer, such as those described above. In this embodiment, the volume of reaction solution and the concentration of reactants is not critical, and can readily be determined by those skilled in the art.

The reaction between the polyclonal antibody to $\alpha_1AT$ and the $\alpha_1AT$ in the sample suspected of containing $\alpha_1AT$ is then carried out for a time and at a temperature suitable to cause the $\alpha_1AT$ to complex with the antibody.

Suitable incubation times and temperatures are readily determined by those skilled in the art. According to the present invention, a suitable incubation time ranges from 5 minutes to 18 hours and a suitable incubation temperature ranges from 4° C. to 37° C. A preferred incubation time and temperature is 2 hours at 37° C.

As with the embodiment using only polyclonal antibodies, a particularly preferred embodiment when the steps are performed out of order is the "paddle embodiment".

After completion of this incubation, the complex is purified.

If the first-species-of-animal antibody to $\alpha_1AT$ is already adhered to a solid substrate, then the purification is accomplished by rinsing the wells or other solid substrate as above, with a suitable buffer such as PBS-TWEEN, or other blocking buffer as described above.

If the first-species-of-animal antibody to $\alpha_1AT$ is not yet adhered to a solid substrate, then the complex is purified by methods known to those skilled in the art, including membrane filtration, precipitation, or adsorption on an antibody coated substrate. For further reaction in solution the complex is resuspended in a suitable blocking buffer such as those described above. In this embodiment, the concentration of the complex in solution is not critical, and suitable concentrations are readily determined by the skilled artisan.

The third reaction step, step (3), of the assay involves reacting a second-species-of-animal antibody to $\alpha_1AT$ with the $\alpha_1AT$ in a sample suspected of containing $\alpha_1AT$.

In order to conduct the third reaction step of the assay the second-species-of-animal antibody to $\alpha_1AT$ is diluted in a suitable reagent such as PBS-TWEEN, or other buffer used in step (2) to a concentration determined empirically from titration curves (dilution vs. OD) and may range from 1.5 $\mu$g/ml to 30 $\mu$g/ml and may comprise a dilution of antiserum of from 1:2000 to 1:100.

If the $\alpha_1AT$ has already been reacted such that it is in a complex adhered to a solid substrate, the second-species-of-animal antibody to $\alpha_1AT$ is added to the well or other solid substrate in a suitable buffer, such as the blocking buffers described above, and generally in the same volume as was used for the first-species-of-animal antibody and $\alpha_1AT$ sample.

If the reaction is being conducted in solution, without one of the reactants comprising a solid substrate, then the reactants are combined in a suitable blocking buffer such as those described above. In this embodiment, the volume of reaction solution and the concentration of reactants is not critical, and can readily be determined by those skilled in the art.

Incubation is then conducted for a time and at a temperature sufficient to form a complex between the $\alpha_1AT$ and the second-species-of-animal antibody to $\alpha_1AT$.

A suitable incubation time and temperature can also be readily determined by those skilled in the art. For example, a suitable incubation time ranges from 5 minutes to overnight, and a suitable incubation temperature ranges from 4° C. to 37° C. A preferred incubation time and temperature is 2 hours at 37° C.

As with the above reaction, this reaction is also conducted in a humidified chamber, under the conditions described above for step (1).

After completion of this incubation, the complex is purified.

If the $\alpha_1AT$ is in a complex already adhered to a solid substrate, then purification is accomplished by rinsing the wells or other solid substrate as above, with a suitable buffer such as PBS-TWEEN, or other blocking buffer as used in step (2).

If the $\alpha_1AT$ is not yet in a complex adhered to a solid substrate, then the complex including the second-species-of-animal antibody to $\alpha_1AT$ is purified by methods known to those skilled in the art, as described above (e.g. membrane filtration, precipitation, etc.). For further reaction in solution, the complex is resuspended in a suitable blocking buffer such as those described above. Further, as described above, the concentration of the complex in solution is not critical, and suitable concentrations are readily determined by the skilled artisan.

The antibody used in the third step may be unlabelled, or may be labelled with an enzyme, radioactive substance label, fluorescent substance label, linking substance, etc.

If the antibody used in the third step of the assay is labelled, the fourth step designated "(4')", comprises detecting the amount of labelled second-species-of-animal antibody in the final complex adhered to the substrate, as described in more detail below.

If the antibody used in the third step of the assay is unlabelled, the fourth step, designated "(4)", of the assay comprises reacting a labelled antibody which is derived from the same species of animal as the antibody used in the first step of the reaction and specific to any antibody from animal species from which the second-species-of-animal antibody was derived with a second-species-of-animal antibody to $\alpha_1$AT such that the two antibodies become complexed. An antibody from a third species of animal could be used for the labelled antibody in this step, but use of an antibody from the first species of animal is strongly preferred due to possible contamination of antibody from a third species of animal with antibody specific to antibody from the first species of animal.

This fourth step of the assay is conducted in the same manner and under the same conditions as described above for the assay using only polyclonal antibody to $\alpha_1$AT.

According to the final step of the assay, the amount of complexed labelled antibody is detected by a method suitable for the type of label used. This is step (4') of the assay using a labelled second-species-of-animal antibody to $\alpha_1$AT and step (5) of the assay using a labelled antibody comprising a first-species-of-animal antibody to an antibody from a second species of animal.

According to the assay using at least one monoclonal antibody to $\alpha_1$AT, the $\alpha_1$AT may be from any mammalian source. Suitable mammalian sources include those mentioned previously for the assay using only polyclonal antibody to $\alpha_1$AT. A preferred source is human-$\alpha_1$AT.

Of course, both the first-species-of-animal antibody to $\alpha_1$AT used in the first reaction step of the assay and the second-species-of-animal antibody to $\alpha_1$AT used in the second reaction step of the assay are antibodies to the particular $\alpha_1$AT to be assayed. Thus, for example, if the $\alpha_1$AT is human-$\alpha_1$AT, then the polyclonal antibody or the monoclonal antibody are antibodies to human-$\alpha_1$AT.

As already mentioned, according to this embodiment of the invention, at least one antibody in either type of assay must be a monoclonal antibody.

For the embodiment wherein the second-species-of-animal antibody to $\alpha_1$AT, i.e. the antibody in step (3), is not labelled, if the first-species-of-animal antibody to $\alpha_1$AT is a monoclonal antibody, the second-species-of-animal antibody to $\alpha_1$AT can be a polyclonal antibody or a monoclonal antibody and visa versa, provided that the two antibodies to $\alpha_1$AT are derived from different species of animals. For example, if both antibodies are monoclonal antibodies and the first species of animal is a mouse, the second species of animal could be a rat. Further, the two antibodies must be directed to different portions of the $\alpha_1$AT molecule so that an antibody-antigen-antibody sandwich can be formed. This is generally not a problem when one of the two antibodies is a polyclonal antibody but is an important consideration when using two monoclonal antibodies.

Further, in this embodiment, for any of the above combinations of antibodies to $\alpha_1$AT, the labelled antibody can be either a monoclonal or polyclonal antibody. However, for practical purposes, if the second species of animal is a mouse or rat or other small animal from which it is difficult to obtain large quantities of antibody, then the labelled antibody would be a monoclonal antibody, since these can easily be obtained in quantities sufficient to conduct the assay.

In this assay, it is preferred that the first-species-of-animal antibody to $\alpha_1$AT and to the second species of antibody be polyclonal antibodies and that the second-species-of-animal antibody be a monoclonal antibody, preferably a mouse monoclonal antibody.

For the embodiment wherein the second-species-of-animal antibody to $\alpha_1$AT, i.e. the antibody in step (3), is labelled, a monclonal antibody can be used for either the first-species-of-animal antibody to $\alpha_1$AT, or the second-species-of-animal antibody to $\alpha_1$AT, or for both antibodies.

If monoclonal antibodies are used for both antibodies, which is a particularly preferred embodiment, it is important to make sure that the antibodies are directed to different portions of the $\alpha_1$AT molecules so that an antibody-antigen-antibody sandwich can be formed.

Preferably, the second-species-of-animal antibody is a mouse monoclonal antibody.

Further in accordance with the assay using at least one monoclonal antibody, the species of animal from which polyclonal antibody is isolated can be any warm blooded animal including goats, sheep, rabbits, mice or equines, etc.

Further, the species of animal from which monoclonal antibody is isolated can be the same as those from which polyclonal antibody is isolated, provided that a suitable myeloma cell line is available, such as myeloma cell lines from mice, rats and humans.

However, if the assay is the one wherein the second-species-of-animal antibody in step (3) is unlabelled, then the second species of animal cannot be the animal used to produce the first-species-of-animal antibody to $\alpha_1$AT.

If the assay is the assay wherein the second-of-animal antibody in step (3) is labelled, then the second-species-of-animal can be the same as the first-species-of-animal or different from the first-species-of-animal.

According to the present invention, a preferred first species of animal for producing polyclonal antibodies is a goat.

A preferred first or second species of animal for producing monoclonal antibodies is a mouse.

Isolation of polyclonal antibodies to $\alpha_1$AT or to the second-species-of-animal antibody is carried out according to methods known in the art.

Isolation of monoclonal antibodies to $\alpha_1$AT which can be used in the present assay is described below in the section entitled "Monoclonal Antibody to $\alpha_1$AT".

Isolation of monoclonal antibodies to the second-species-of-animal antibody is carried out according to methods known in the art. Further, numerous such antibodies are commercially available and these are suitable for use in the present invention.

Determination of whether two antibodies react with different portions of the $\alpha_1$AT molecule is by methods known to those skilled in the art.

In the present assay, it is required that the monoclonal antibody to $\alpha_1$AT have substantially no cross reactivity with albumin from the source from which the $\alpha_1$AT to be measured is derived. This is also a requirement for the antibody specific to the second-species-of-animal antibody, if albumin will be present under the reaction conditions for the step wherein this antibody is complexed to the second-species-of-animal antibody.

A preferred monoclonal antibody to $\alpha_1$AT for use in the present invention is one having all the identifying characteristics of the monoclonal antibody produced by hybridoma clone LHAT-1, having ATCC deposit no. HB 9199.

Affinity purified antibody is required for the first-species-of-animal antibodies used in steps (1) and (2) as well as step (4) of the embodiment using labelled antibody comprising a first-species-of-animal antibody to an antibody from a second species of animal. Affinity purification can be performed as mentioned above with respect to the assay using only polyclonal antibodies.

The labelled antibody according to the present invention is produced by complexing a labelling means to the antibody.

The labelling means or label used to label the antibody can be one of numerous labels known to those skilled in the art and include those listed above such as enzyme labels, radioactive substance labels and fluorescent labels, etc.

According to the assay using at least one monoclonal antibody, a preferred label is an enzyme, and a preferred enzyme is peroxidase, especially horseradish peroxidase.

Methods of conjugating the label to the antibody are well known to those skilled in the art as already mentioned above, and these techniques can be equally well used here.

A particularly preferred labelled first-species-of-animal antibody to antibody from a second species of animal for use in the assay using at least one monoclonal antibody is horseradish peroxidase-conjugated goat anti-mouse IgG. The conjugation can be by methods mentioned above.

Detection of the amount of labelled antibody depends upon the type of label, and detection methods are well known to those skilled in the art as already mentioned above.

Also as described above, when the label is peroxidase, a preferred method of detecting the amount of labelled antibody is by using a substrate solution comprising ABTS and $H_2O_2$ as previously described.

According to the assay employing at least one monoclonal antibody, concentrations of human-$\alpha_1$AT as low as 15 ng/ml can be measured.

The samples which can be analyzed in the present assay employing a monoclonal antibody include fluids such as those mentioned above. Also as above, blood serum, synovial fluid, saliva, and bronchoalveolar lavage fluids are especially preferred.

Double Antibody Sandwich Immunosorbent Assay Screening Kit

The present invention in an even further embodiment provides a double antibody sandwich immunosorbent assay kit to conduct any of the above-described assays.

If the assay to be performed is one wherein the labelled antibody is a labelled first-species-of-animal antibody to antibody from a second species of animal, the kit comprises at least three components:

(1) a first-species-of-animal antibody, either polyclonal or monoclonal, to $\alpha_1$AT;

(2) a second-species-of-animal antibody, either polyclonal or monoclonal, to $\alpha_1$AT; and (3) a labelled antibody, either polyclonal or monoclonal, comprising a first-species-of-animal antibody to antibody from the second species of animal.

If the assay to be performed is one wherein the labelled antibody is a labelled second-species-of-animal antibody to $\alpha_1$AT. the kit comprises at least two components:

(1) a first-species-of-animal antibody, either polyclonal or monoclonal, to $\alpha_1$AT; and (2) a labelled second-species-of-animal antibody, either polyclonal or monoclonal, to $\alpha_1$AT.

Optionally, each kit also includes: (A) a means for detecting the labelled antibody, such as, for example a substrate solution when the label is an enzyme, and/or (B) a solid substrate support for the first-species-of-animal antibody to $\alpha_1$AT.

As with the above described assays, the $\alpha_1$AT can be any $\alpha_1$AT from any of the above-described sources and, preferably is human-$\alpha_1$AT.

As noted above, the assay can be one which employs a polyclonal antibody or a monoclonal antibody as any of the antibodies. The characteristics of the polyclonal antibody and/or monoclonal antibody used in the test kit are the same as those described above for the respective assays.

In a preferred embodiment, when the kit employs a polyclonal antibody as the second-species-of-animal antibody to $\alpha_1$AT, the first-species-of-animal antibody is a goat antibody and the second-species-of-animal antibody is a rabbit. Further, the labelled first-species-of-animal antibody is preferably an enzyme-conjugated anti-rabbit immunoglobulin and most preferably a peroxidase-conjugated goat anti-rabbit IgG. Also preferred is a kit wherein the first-species-of-animal antibody is a goat antibody and the second-species-of-animal antibody is a mouse antibody. When the second-species-of-animal antibody is an unlabelled mouse antibody, the preferred labelled first-species-of-animal antibody is an enzyme-conjugated anti-mouse immunoglobulin and, most preferably, a peroxidase-conjugated goat anti-mouse IgG. especially a horseradish peroxidase-conjugated goat anti-mouse IgG.

When the kit is designed for conducting the assay which uses a second-species-of-animal monoclonal antibody to $\alpha_1$AT. it is preferred that the monoclonal antibody be a monoclonal antibody that has all the identifying characteristics of that produced by hybridoma clone LHAT-1. having ATCC deposit no. HB 9199.

Further, when the assay is an assay using the second-species-of-animal monoclonal antibody and a first-species-of-animal polyclonal antibody, it is preferred that the first-species-of-animal antibody be a goat antibody and the second-species-of-animal antibody be a mouse antibody. If the second-species-of-animal antibody is unlabelled, it is preferred that the labelled first-species-of-animal antibody be an enzyme-conjugated goat anti-mouse antibody and most preferably a peroxidase-conjugated goat anti-mouse IgG, especially horseradish peroxidase-conjugated goat anti-mouse IgG.

The physical form in which the various components of the kit are supplied can be readily determined by those skilled in the art.

Preferably the first-species-of-animal polyclonal antibody to $\alpha_1$AT is provided in a suitable coating buffer with a suitable preservative such as sodium azide, all at concentrations sufficient to perform the intended assays, which can be determined by the skilled artisan in accordance with the requirements of the particular assays.

Preferably the second-species-of-animal antibody, labelled or not, to $\alpha_1$AT is provided in a suitable blocking buffer with a suitable preservative such as sodium azide, all at concentrations sufficient to perform the intended assays, which can be determined by the skilled artisan in accordance with the requirements of the particular assays.

The labelled first-species-of-animal antibody to antibody from the second type of animal is preferably provided in a suitable blocking buffer with a suitable preservative such as sodium azide, all at concentrations sufficient to perform the intended assays, which can be determined by the skilled artisan in accordance with the requirements of the particular assays.

When the label is peroxidase, for example, horseradish peroxidase, the preferred means for detecting the peroxidase-conjugated antibody is the substrate ABTS, which can be provided dry, with 0.2M phosphate buffer (pH 7.6) and $H_2O_2$ provided as separate reagents.

Other means for detecting the labelled antibody can be supplied in a form readily determined by those skilled in the art.

Solid substrate supports for the first-species-of-animal antibody include those mentioned above in the description of the assays.

The assay for the kit is performed as described above for the assay using only polyclonal antibodies or for the assay using at least one monoclonal antibody.

Other conditions, such as shelf life, shipping conditions, cost considerations, etc. can be readily determined by the skilled artisan.

Monoclonal Antibody To $\alpha_1 AT$

A further embodiment of the present invention provides a monoclonal antibody having specific reactivity to $\alpha_1 AT$. the antibody being further characterized in that it exhibits substantially no cross reactivity with albumin from a source from which the $\alpha_1 AT$ to be measured was derived.

According to the present invention, the monoclonal antibody can be produced as follows.

Suitable animals such as mice or rats are immunized intraperitoneally with $\alpha_1 AT$ in a suitable adjuvant. The animals are boosted by further intraperitoneal injection of $\alpha_1 AT$ as needed. This immunization is carried out by methods known to those skilled in the art, using multiple injections of antigen to boost immunoglobulin production.

In the present invention, the preferred animal is a mouse, and more preferably a Balb/c mouse, which is injected first with 100 μg of $\alpha_1 AT$ in saline, emulsified with an equal volume of complete Freund's adjuvant, then boosted two weeks later by a similar quantity of antigen in incomplete Freund's adjuvant,. followed by an injection of antigen alone at least two weeks later, and 3 days before harvesting of the spleen.

After a suitable amount of time has elapsed to allow development of spleen cells producing antibody to $\alpha_1 AT$, the animals are sacrificed and the spleens are prepared for fusion by methods known to those skilled in the art, for example, by the method of Fazekas de St. Groth and Scheidegger, 1980, *J. Immuno. Meth.* 35, 1.

Single cell suspensions of splenocytes are prepared and the red blood cells lysed by methods known to those skilled the art, for example, by expressing splenocytes from the spleen capsule with a sterile garlic press and incubation of the expressed cells for two minutes at 0° C. in ammonium chloride, Tris buffer. (Kennett et al., 1978, *Curr. Top. Microbiol. Immunol.* 81, 71–79).

After lysis,. the splenocytes are centrifuged and resuspended in a suitable serum-free medium, such as Dulbecco's modified Eagle's medium.

The donor splenocytes are then mixed with appropriate recipient myeloma cells, such as from mice or rats, for fusion according to methods known in the art. Suitable recipient mouse myeloma cells include P3×63Ag, P3×63Ag8.653, NS1, Sp2/0-Ag14. and P3U1.

In the present invention, when splenocytes from Balb/c mice are used, it is preferred that the myeloma cells be Balb/c plasmacytoma cells which have been selected to be a non-secreting, non-producing continuous cell line, lacking the enzyme hypoxanthine phosphoribosyl transferase (HPRT−) and thereby sensitive to 8-azaguanine. The preferred line in the present invention is the cell line P3×63Ag8.653 plasmacytoma cells, available from ATCC (Kearney et al, 1979, *J. Immunol.* 123, 1548–1550.) Approximately one hundred million splenocytes are mixed with $10^7$ plasmacytoma cells.

Fusion is performed by any of the methods known to those skilled in the art. For example, the mixed cell pellet of splenocytes and plasmacytoma may be briefly treated with fusogen such as Sendai virus, polyethylene glycol (PEG) or lysophosphatidylcholine.

In the present invention, it is preferred that fusion be performed with a specially prescreened batch of polyethylene glycol, for example PEG 4000 from Merck, Darmstadt, Germany, which is minimally cytotoxic at concentrations of 30–50% (v/v). The mixed cell pellet is slowly and gently mixed with an equal volume of 50% PEG 4000 at room temperature for 30 seconds, followed by gradual careful addition of 5 ml of serum-free medium over a 5 minute period to gently dilute the fusogen from the cells.

After fusion, the cells are cultured in a selective medium such as hypoxanthine-aminopterin-thymidine (HAT) toxic to unfused plasmacytoma cells deficient in the HPRT enzyme, according to methods known to those skilled in the art until hybridoma clones become visible (Duvic et al, 1985. *J. Lipid Res.* 26, 540–548.).

The hybridoma clones are then screened either by a modified double sandwich ELISA for $\alpha_1 AT$ purified from the immunogen according to the assay described and claimed herein or by a direct ELISA as described in the Examples herein. Positive hybridoma clones are identified by development of color in ELISA assay of supernatant culture fluids, and then subcloned by limiting dilution in tissue culture plates, and retested by the ELISA.

Clones identified as reacting in the screening methods are then further tested for extent of specificity for $\alpha_1 AT$ and then tested for cross reactivity to albumin using a modified double antibody sandwich ELISA for albumin described in the Examples herein or by methods known to those skilled in the art (Mancini, G., A. O. Carbonara and J. F. Heremans, 1965, *Int. J. Immunochem.* 2, 235).

The monoclonal antibody is isolated from the hybridoma by methods known to those skilled in the art. For routine assays, the supernatant culture medium is harvested from the hybridoma culture, centrifuged at low speed to remove cells, and frozen. The antibody in this medium is stable under refrigeration or freezing for 2 years or more.

The antibody isotype can be determined by Ouchterlony double diffusion using standard, commercially available antisera to mouse immunoglobulins, such as is available from Cappel Laboratories. In the present invention, the isotype of the immunoglobulin derived from hybridoma clone LHAT-1, having ATCC deposit no. HB 9199, was determined to be IgG1(kappa).

Alternately, in the case of an IgG1 immunoglobulin, the antibody fraction can be separated from the culture medium on a column of solid-phase protein A from Staphylococcus aureus. Goding. James W. *Monoclonal Antibodies: Principles and Practice*, Academic Press, N.Y., 1983.

Alternate methods for isolating other immunoglobulin isotypes are known to those skilled in the art and include affinity purification on a solid phase antibody column (Ax'en R. J. Porath, and S. Ernback, 1967, *Nature* 214. 1302: Cuatrecasas P. and C. B. Anfinsen, 1971, *Annv. Rev. Biochem.* 40. 259.), etc.

According to the above method, a monoclonal antibody having specific reactivity to $\alpha_1$AT, and exhibiting substantially no cross reactivity with albumin from the source of the $\alpha_1$AT, can be obtained.

By exhibiting substantially no cross reactivity with albumin, it is meant that the cross reactivity with albumin, as assayed in a double antibody sandwich ELISA for albumin (See Examples herein). is an OD less than 0.100 at a 1:100 dilution.

In a preferred embodiment, the monoclonal antibody is produced to human-$\alpha_1$AT and has substantially no cross reactivity with human albumin.

One such monoclonal antibody which has been isolated is produced by a hybridoma clone designated LHAT-1 which is deposited at the American Type Culture Collection, Rockville, Md., and has ATCC deposit no. HB 9199.

Hybridoma Capable Of Producing Monoclonal Antibody That Reacts With $\alpha_1$AT And Does Not Cross React With Albumin The present invention also provides a hybridoma capable of producing the above-described monoclonal antibody.

The hybridoma is produced and isolated according to the procedure described above.

In order to propagate the hybridoma, suitable culture conditions and a suitable culture medium are used which can be readily determined by those skilled in the art.

According to the present invention, suitable culture conditions comprise continuous cell culture in suspension at 37° C. in a 95% air/5% $CO_2$ atmosphere, and a suitable medium comprises Dulbecco-modified Minimum essential Medium. Eagle (DMEM) with L-glutamine. 1 g/l D-glucose, sodium pyruvate (Grand Island Biological catalog number 430–1600) supplemented with 10% (v/v) heat-inactivated fetal calf serum (Grand Island catalog number 230-6140), 2 mM L-glutamine. 1 mg/ml sodium bicarbonate, and 0.0075% (v/v) mercaptoethanol. Cells are initially cultured at a density of $3 \times 10^5$ cells per ml in 20 ml contained in a 75 cm$^2$ tissue culture flask, and subcultured by dilution into fresh medium after 3 to 4 days, when a density of about $1.5 \times 10^6$ cells per ml may be routinely obtained.

Periodically, continuous cultures should be renewed by restarting cultures from frozen stocks, cells are frozen as soon as possible after initial cloning or subcloning by low speed centrifugation and resuspension of the cells in 90% fetal calf serum/10% dimethyl sulfoxide (v/v) at 0° C., followed by slow freezing of the cells in a −70° C. ultracold freezer within a styrofoam container. The frozen cells are then rapidly immersed in liquid nitrogen and kept under liquid nitrogen until thawing.

In the present invention, LHAT-1 cells thus frozen may be recovered with greater than 90% viability by methods known to those skilled in the art, and replace stocks in continuous culture within 2 weeks.

The following examples are given to illustrate the present invention in greater detail but these examples are not to be construed as limiting the scope of the present invention. Unless otherwise indicated, all parts, percents, ratios and the like are by weight. All dilutions noted are by volume unless otherwise indicated.

EXAMPLE 1

The sensitivity of the ELISA using polyclonal antibodies to $\alpha_1$AT is demonstrated here as follows and the sensitivity of the ELISA to the sensitivity of the radial immunodiffusion assay is compared.

Double Antibody Sandwich ELISA using Polyclonal Antibody to Alpha-1-Antitrypsin (1) Biological Samples The sera used in these studies were prepared by allowing blood obtained by venipuncture to clot at room temperature in a glass tube. The sera were aliquoted and frozen at −70° C. until assay an were subjected to only one freeze-thaw cycle. The $\alpha_1$AT phenotype of each serum was determined by isoelectric focusing as described (Allen, R. C. R. A. Harley and R. C. Talamo. 1974 *Am. J. Clin. Pathol.* 62. 732) using an LKB Multiphor system (produced by LKB, Inc.. Rockville. MD) and ultrathin layer electrofocusing gels (pH 4–5) obtained from Accurate Chemical Company (Westbury. N.Y.). Synovial fluid samples from humans were collected by aspiration for clinical indications. Cells and debris were removed immediately by centrifugation and the samples stored at −20° C. Parotid saliva samples were collected from humans during a gustatory stimulus with lemon juice as described in Daniels. T. E., S. Silverman Jr., J. P. Michalski, J. S. Greenspan. R. A. Sylvester and N. Talal, 1975. *Oral Surg.* 39, 875, and stored at −20° C. Healthy nonsmoking volunteers and smokers hospitalized for workup of nonmalignant pulmonary nodules had bronchoalveolar lavage isolated by standard techniques (Basar. Y., R. D. DeShazo. H. Barleman and J. Nordberg. 1982. *Chest* 82. 323). Cells were removed from the lavage fluid by centrifugation and the fluid was stored at −70° C. until used (DeShazo, R. D., D. E. Banks. J. E. Diem. J. A. Nordberg. Y. Baser, D. Salvaggio 1, and J. E. Salvaggio. 1983. *Am. Rev. Respir. Dis.* 127, 545).

(2) Radial Immunodiffusion

Serum and synovial fluid samples were assayed for $\alpha_1$AT by radial immunodiffusion according to methods known in the art, such as that described in Mancini, G., A. O. Carbonara, and J. F. Heremans. 1965, *Int. J. Immunochem.* 2, 235. Kallestad (Austin, TX) 24-well Quantiplates (lot nos. 69531 and 66142). "RID plates", standards and samples were equilibrated to room temperature and 5-$\mu$l aliquots of standards or samples were dispensed into the wells. The plates were incubated for 18 hours (h) at room temperature and the diameter of the precipitin ring was measured using a calibrating RID viewer distributed by Kallestad and manufactured by Transidyne General Corporation (Ann Arbor. Mich.). The $\alpha_1$AT concentration for each sample was determined from a standard curve plotted on semilog paper.

(3) ELISA Supplies and Reagents

The ELISA was performed in 96-well disposable flat-bottomed polyvinyl chloride plates (Dynatech, Alexandria, Va.). Goat polyclonal anti-human $\alpha_1$AT was obtained from Cooper Biomedial (Malvern, Pa.). Rabbit anti-human $\alpha_1$AT and affinity-purified goat anti-rabbit IgG-peroxidase conjugate were both obtained from Boehringer Manheim (Indianapolis, Ind.). Both antibodies to $\alpha_1$AT were prepared from highly purified antigens, were adsorbed to remove nonspecific antibodies and were shown to be monospecific by immunoelectrophoresis against human plasma. Salt-free chromatographically prepared human $\alpha_1$AT was obtained from Sigma Chemical Co. (St. Louis. Mo.) and was reconstituted in phosphate-buffered saline (pH 7.45) at a concentration of 10 mg/ml for use in recovery. ABTS (2,2'-azino-di-(3-ethylbenzthiazoline sulfonic acid)) was obtained from Sigma Chemical Co. A solution of 1 mg/ml ABTS in 0.2M phosphate buffer (pH 7.6) plus 0.003% $H_2O_2$ was used as the substrate. Carbonate/bicarbonate buffer (pH 9.6) was used as the binding buffer for the coating antibody. The carbonate/bicarbonate buffer was made as follows: Sol'n A: 0.2M solution of anhydrous sodium-1.696 g anhydrous $Na_2CO_3+80$ ml deionized distilled water: Sol'n B: 0.2M solution of sodium bicarbonate-2.856g $NaHCO_3+170$ ml deionized distilled water. A and B were mixed together and enough deionized distilled water was added to bring the volume to 1 liter. The pH was adjusted to 9.6. All other reagent dilutions and washes were made with phosphate-buffered saline (pH 7.45) with 0.05% TWEEN 20 (PBS-TWEEN). The PBS-TWEEN comprised 8.0 g NaCl, 0.2 g $KH_2PO_4$, 2.9 g $Na_2HPO_4.12\ H_2O$, 0.2 g KCl and 0.5 ml TWEEN 20 dissolved in 1 liter of water.

(4) Modified Double Antibody Sandwich ELISA

A standard serum sample (phenotype MM) with an $\alpha_1$AT concentration of 2.45 mg/ml was diluted and run as a standard curve for each assay in a range of dilutions of from 3 to 1000 ng/ml. The reagents and samples were added sequentially to the microplate wells as described below. After each incubation, the wells were rinsed 3 times with PBS-TWEEN. In the initial step, goat polyclonal anti-human $\alpha_1$AT was diluted in carbonate/bicarbonate buffer at a concentration of 25 $\mu$g/ml and 100 $\mu$l of antibody was added to each well followed by overnight incubation at 4° C in a humidified chamber. Samples and standards were diluted in PBS-TWEEN according to their likely concentration as described below. 100 $\mu$l of diluted sample was added to each antibody-coated well followed by a 2 h incubation at 37° C. Rabbit anti-human $\alpha_1$AT was diluted 1:1000 in PBS-TWEEN and 100 ul was added to the wells followed by incubation at 37° C. for 2 hours in a humidified chamber.

Peroxidase-conjugated goat anti-rabbit IgG was diluted 1:200 in PBS-TWEEN and 100 $\mu$l added to each well. After 2 hours incubation at room temperature, 100 $\mu$l of substrate solution (1 mg/ml ABTS and 0.003% $H_2O_2$) was added for 30 min at room temperature. The optical densities were read at 410 nm using an MS 320 Dynatech microplate reader. Background optical density measured in the absence of $\alpha_1$AT was less than 1.0% of the maximum optical density.

Figure 2:
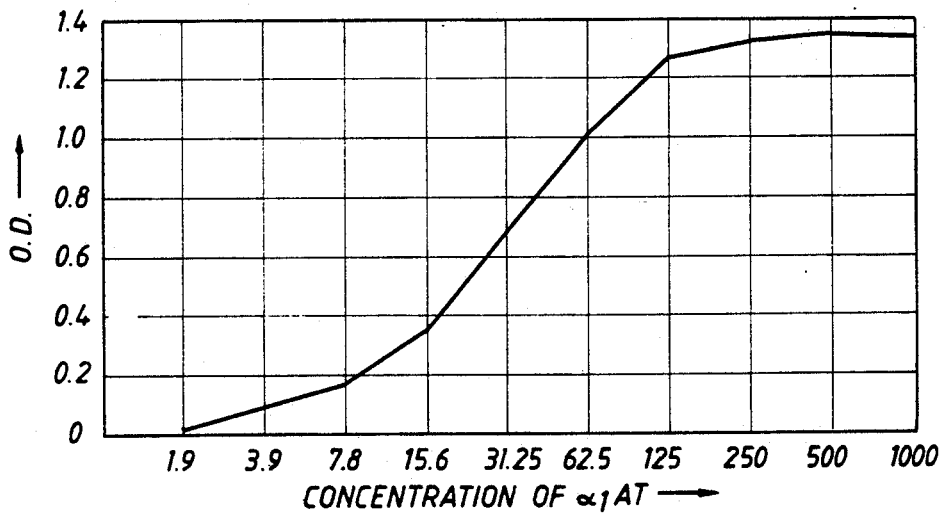
FIG. 2 is a standard curve for alpha-1-antitrypsin measured by an ELISA of this invention using polyclonal antibodies plotted on a semilog scale. Abscissa: 2-fold dilutions of serum expressed as ng/ml of $\alpha_1$AT: ordinate: optical density at 410 nm.

The concentration of $\alpha_1$AT was determined for multiple 2-fold dilutions of each sample by comparison to a standard curve plotted on log/log paper (FIG. 1). The dilutions were chosen to encompass the steep linear portion of the curve as plotted on semilog paper (FIG. 2). The original concentration of the sample was calculated by multiplying the $\alpha_1$AT concentration of the diluted sample by the dilution factor. Because of the wide variation in the concentration of $\alpha_1$AT in various biological fluids, generally the approximate range of the sample was identified by assaying consecutive 10-fold dilutions and then more precisely quantitating the concentration with an assay using appropriately chosen 2-fold dilutions. For example, when the approximate concentration of $\alpha_1$AT in the sample was known, five or six 2-fold dilutions were made, chosen to encompass the range of 7.8 to 125 ng/ml.

(5) Determination of Optimum Antibody Concentrations for the Assay

Goat polyclonal anti-human $\alpha_1$AT was tested at 100, 50, 25, 10 and 1 $\mu$g/ml, rabbit anti-human $\alpha_1$AT at 1:100, 1:200, 1:500, 1:1000 and 1:2000, and peroxidase-conjugated goat anti-rabbit IgG at 1:100, 1:200, 1:500 and 1:1000. Saturation curves were drawn (dilution vs OD) and the optimum dilution for each antibody was selected as reported above.

(6) Measurement of $\alpha_1$AT in Serum by the Modified Double Antibody Sandwich ELISA Dilutions of serum from 1:1250 to 1:640,000 were made and the ELISA performed as described. A plot of 2-fold dilutions of serum concentration against the log of the optical density demonstrated a linear relationship over a wide range of concentrations (FIG. 1). When the optical density was plotted on an arithmetic scale, a typical sigmoid curve was observed with 3–4 points falling on a roughly linear central segment with a steep slope (FIG. 2). Similar curves were run for each assay using a standard serum sample. In all of the experiments, the linear segment occurred either between 15.68 and 125 ng/ml (concentration of the diluted standard) as shown in FIG. 2, or more frequently between concentrations of 7.8 and 62.5 ng/ml.

To compare the ELISA assay to a standard RID method, $\alpha_1$AT levels in each serum sample were determined by radial immunodiffusion. Sera was chosen with a wide range of concentrations and measured by RID and the quantity of $\alpha_1$AT was calculated for each of several points in the central segment of the curve, as shown in Table I below. Similar concentrations were found at several different dilutions, and the best concordance between consecutive dilutions occurred in the steeply rising segment of the dilution/OD curve. The dilutions presented in Table I reflect this. The ELISA results correlated closely with data from a standard RID method. In addition, the ELISA quantified the $\alpha_1$AT in serum from several subjects having concentrations that were below the limit of sensitivity of the RID method.

TABLE I

CONCENTRATION OF $\alpha_1$AT ($\mu$g/ml) IN SERUM DETERMINED BY ELISA AND RADIAL IMMUNODIFFUSION

| Sample | Dilution ($\times 10^3$) | | | | | | | RID |
|---|---|---|---|---|---|---|---|---|
| | 10 | 20 | 30 | 40 | 80 | 160 | 320 | |
| 1 | 420[a] | 390 | — | 372 | — | — | — | <720[b] |
| 2 | 370 | 350 | 381[c] | — | — | — | — | <720 |
| 3 | 950 | 820 | — | 760 | 720 | — | — | <720 |
| 4 | 1250 | 1320 | — | 1360 | 1256 | — | — | 1350 |
| 5 | —[d] | 860 | — | 1160 | 1120 | — | — | 1150 |

TABLE I-continued

CONCENTRATION OF $\alpha_1$AT ($\mu$g/ml) IN SERUM DETERMINED BY ELISA AND RADIAL IMMUNODIFFUSION

| Sample | Dilution ($\times 10^3$) | | | | | | | RID |
|---|---|---|---|---|---|---|---|---|
| | 10 | 20 | 30 | 40 | 80 | 160 | 320 | |
| 6 | — | — | — | 2000 | 2400 | 2496 | 2496 | 2700 |
| 7 | — | — | — | — | 4240 | 4160 | 3840 | 3500 |

[a] Calculated concentration in $\mu$g/ml compared to a standard serum sample.
[b] Subjects 1-4 had genetic variants of $\alpha_1$AT or severe illness associated with decreased serum levels. Sample 1 was from a subject prepared for bone marrow transplantation for leukemia. Sample 2, ZZ phentotype; sample 3-4, MZ; sample 5-7, MM.
[c] Only sample 2 was run at a 1:30,000 dilution.
[d] OD of dilution outside steep portion of curve.

(7) Determination of $\alpha_1$AT in Synovial Fluid By ELISA

Measurement of $\alpha_1$AT in synovial fluid also demonstrated correlation among concentrations calculated for consecutive 2-fold dilutions (Table II). These values were usually higher than those determined by radial immunodiffusion but better reflect the true concentration of $\alpha_1$AT in synovial fluid because of interference caused by hyaluronic acid and the slower diffusion of complexes of $\alpha_1$AT with proteolytic enzymes found in the synovial space (Robinson. A. D., K. N. Boyden, S. M. Hendrickson and K. D. Muirden. 1981, *J. Rheumatol*, 8, 548). Two samples (6 and 7) were found to have slightly higher concentrations by RID than ELISA.

Samples 8, 9. 12. 13 and 15 were from patients with inflammatory arthritis and had a mean synovial fluid white blood cell count of 26,770 cells/mm$^3$ and a mean $\alpha_1$AT (by ELISA) of 1773 g/ml. Samples 10. 11 and 14 were noninflammatory and had a mean white blood cell count of 1446 cells/mm$^3$ and a mean $\alpha_1$AT concentration of 1483 ug/ml. Simultaneously drawn serum samples were available for 6 of the 8 patients and the serum $\alpha_1$AT concentration (determined by RID) is recorded in the last column of Table II below.

TABLE II

CONCENTRATION OF $\alpha_1$AT ($\mu$m/ml) IN SYNOVIAL FLUIDS DETERMINED BY ELISA AND RADIAL IMMUNODIFFUSION

| Sample | Dilution ($\times 10^3$) | | | | Mean[b] | RID[c] | Serum[d] |
|---|---|---|---|---|---|---|---|
| | 20 | 40 | 80 | 160 | | | |
| 8 | 2500[a] | 2800 | 2760 | 2920 | 2745 | 2040 | 2300 |
| 9 | 1300 | 1520 | 1540 | 1760 | 1530 | 800 | 1280 |
| 10 | 1520 | 1220 | 1260 | 1410 | 1350 | 1300 | 1700 |
| 11 | 2400 | 2560 | 2000 | 2000 | 2240 | 1500 | 1830 |
| 12 | 1040 | 1000 | 1200 | 1280 | 1130 | 1080 | 1480 |
| 13 | 2000 | 2000 | 1880 | 2000 | 1970 | 2350 | NA[e] |
| 14 | 880 | 820 | 880 | — | 860 | 980 | NA |
| 15 | 1640 | 1360 | 1440 | 1520 | 1490 | 1300 | 2050 |

[a] Calculated concentration in $\mu$g/ml compared to standard serum sample.
[b] Mean concentration determined by ELISA.
[c] Concentration determined by radial immunodiffusion.
[d] Serum $\alpha_1$AT concentration determined by RID.
[e] Serum sample not available for study.

(8) Modified Double Antibody Sandwich ELISA Measurements of Known Quantities of $\alpha_1$AT Added to Synovial Fluid Samples Biological fluids such as synovial fluid could interfere with the accurate determination f $\alpha_1$AT by the ELISA. The concentration in known amounts of $\alpha_1$AT added to synovial fluid were measured. Two replications were performed using synovial fluids adding 2-6 times the starting concentration as shown in Table III below and measuring the recovered $\alpha_1$AT both by ELISA and RID. The ELISA measured all of the added $\alpha_1$AT whereas the RID determined only about 60-70%.

TABLE III

EFFECT OF SYNOVIAL FLUID ON DETECTION BY ELISA AND RID OF ADDED $\alpha_1$AT

| Sample | Added $\alpha_1$AT ($\mu$g/ml) | $\alpha_1$AT conc. by ELISA ($\mu$g/ml) | % Recovery (ELISA) | $\alpha_1$AT conc. by RID ($\mu$g/ml) | % Recovery (RID) |
|---|---|---|---|---|---|
| A + | None | 820[a] | — | 960 | — |
| A + | 1500 | 2500 | 112 | 1900 | 64 |
| A + | 3000 | 3870 | 101 | 2900 | 65 |
| A + | 6000 | 7440 | 110 | 4900 | 66 |
| B + | None | 1100 | — | 850 | — |
| B + | 1500 | 2720 | 108 | 2100 | 83 |
| B + | 3000 | 4800 | 123 | 2600 | 58 |
| B + | 6000 | 7340 | 104 | 4900 | 68 |

[a] Calculated concentration in $\mu$g/ml compared to a standard serum sample.

(9) Determination of $\alpha_1$AT Concentrations in Saliva by ELISA

Of the several biological fluids the lowest concentrations of $\alpha_1$AT were found in parotid gland saliva collected directly from Stenson's duct. Two samples had a mean of less than 1 $\mu$g/ml (275 and 353 ng/ml) and were measured at dilutions of 1:2–1:16 as shown in Table IV below. Two additional samples, with mean concentrations of 2.8 $\mu$g/ml and 1.7 $\mu$g/ml, were best determined at dilutions between 1:20 and 1:320. These measurements demonstrate the usefulness of the double antibody sandwich ELISA of this invention in determining $\alpha_1$AT levels in saliva or other similar secretions with very low concentrations of $\alpha_1$AT.

TABLE IV

CONCENTRATION OF $\alpha_1$AT ($\mu$g/ml) IN PAROTID SALIVA DETERMINED BY ELISA

| Sample | Dilution | | | |
|---|---|---|---|---|
| | 1:2 | 1:4 | 1:8 | 1:16 |
| 16 | 0.24[a] | 0.27 | 0.29 | 0.30 |
| 17 | 0.25 | 0.46 | 0.34 | 0.36 |
| | 1:40 | 1:80 | 1:160 | 1:320 |
| 18 | 2.80 | 2.32 | 2.80 | 2.80 |
| 19 | — | 1.60 | 1.84 | 1.70 |

[a] Concentration in $\mu$g/ml compared to a standard serum sample.

Two replications were performed (as described above) using saliva samples with different starting concentrations and adding approximately 10-, 20- and 40-fold excesses of purified $\alpha_1$AT. as shown in Table V below. The recovery of $\alpha_1$AT (by ELISA) with sample C was virtually 100% and for the second sample was 75-85%.

TABLE V

EFFECT OF SALIVA ON DETECTION BY ELISA OF ADDED $\alpha_1$AT

| Sample | | Added $\alpha_1$AT ($\mu$g/ml) | $\alpha_1$AT Conc by ELISA ($\mu$g/ml) | % Recovery |
|---|---|---|---|---|
| C | + | None | 0.22[a] | — |
| C | + | 2.5 | 2.60 | 95.0 |
| C | + | 5.0 | 5.50 | 105.6 |
| C | + | 10 | 9.35 | 91.3 |
| D | + | None | 1.7 | — |
| D | + | 25 | 23.1 | 85.6 |
| D | + | 50 | 39.2 | 75.0 |
| D | + | 100 | 76.0 | 76.0 |

[a]Concentration compared to a standard serum sample calculated as the mean of 3 dilutions in the central segment of the dilution curve.

(10) Measurement of $\alpha_1$AT in Bronchoalveolar Lavage Fluids by ELISA $\alpha_1$AT is important physiologically in the lung. Studies of $\alpha_1$AT in the bronchoalveolar lavage fluids (BAL) in the past have been complicated because the insensitivity of prior art available assays for $\alpha_1$AT required concentration of the lavage fluid with loss of significant quantities of the protein (see Olsen. G. N., J. O. Harris. J. R. Castle, R. H. Welchman and H. J. Karmgard, 1975. *J. Clin. Invest.* 55. 427; Stone. P. J., J. D. Calore. S. E. McGowan, J. Bernardo. G. L. Strider and C. Oranzblau. 1983. *Science* 221. 1187).

In contrast, the sensitivity of the double antibody sandwich ELISA method of this invention allows measurement of $\alpha_1$AT in BAL fluids without concentration, and in most cases involves a 50- to 100-fold dilution. Eight fluids obtained from normal individuals demonstrated 6 with $\alpha_1$AT concentrations comparable to those previously reported (Olsen. G. N., J. O. Harris. J. R. Castle. R. H. Welchman and H. J. Karmgard. 1975. *J. Clin. Invest.* 55, 427; Stone, P. J., J. D. Calore. S. E. McGowan, J. Bernardo, G. L. Strider and C. Oranzblau, 1983, *Science* 221, 1187) for concentrated samples (Table VI). Two of the 8 samples (samples 26 and 27) were significantly lower than 1 $\mu$g/ml and were best quantified at a lower dilution.

TABLE VI

CONCENTRATION OF $\alpha_1$AT ($\mu$g/ml) IN BRONCHIAL LAVAGE FLUIDS DETERMINED BY ELISA

| Sample | Dilution | | | | Mean |
|---|---|---|---|---|---|
| | 1:50 | 1:100 | 1:150 | 2:200 | |
| 20 | 2.30[a] | 2.23 | 2.34 | 2.30 | 2.29 |
| 21 | 1.85 | 1.63 | 1.50 | 1.60 | 1.65 |
| 22 | 1.22 | 2.24 | ND[b] | 2.10 | 1.85 |
| 23 | 2.00 | 1.30 | 1.23 | 1.28 | 1.45 |
| 24 | 1.47 | 1.24 | ND | 1.24 | 1.32 |
| 25 | 0.80 | 0.78 | —[c] | — | 0.79 |
| | 1:10 | 1:20 | 1:50 | | |
| 26 | 0.16 | 0.13 | 0.20 | | 0.16 |
| 27 | — | 0.31 | 0.36 | | 0.34 |

[a]Calculated concentration in $\mu$g/ml compared to a standard serum sample.
[b]Not determined.
[c]Outside linear segment of curve.

Albumin concentrations were determined in 5 of the BAL fluids, using a modified double antibody sandwich ELISA. The concentration of albumin was found to be 46.4±7 $\mu$g/ml (mean±SE) and the $\alpha_1$AT of the samples expressed as $\mu$g/mg of albumin was 32.8±12.2 (mean±SE).

Determination with 2 BAL fluids of added $\alpha_1$AT showed virtually complete determination of 1.5 and 20 $\mu$g/ml of added $\alpha_1$AT as shown in Table VII.

TABLE VII

EFFECT OF BRONCHOALVEOLAR LAVAGE FLUID ON DETECTION OF $\alpha_1$AT BY ELISA

| Sample | | Added $\alpha_1$AT ($\mu$g/ml) | $\alpha_1$AT Conc. by ELISA ($\mu$g/ml) | % Recovery |
|---|---|---|---|---|
| E | + | None | 0.94[a] | — |
| E | + | 1 | 2.18 | 124 |
| E | + | 5 | 5.69 | 95 |
| E | + | 20 | 20.53 | 98 |
| F | + | None | 1.28 | — |
| F | + | 1 | 2.34 | 106 |
| F | + | 5 | 5.65 | 87 |
| F | + | 20 | 21.95 | 103 |

[a]Concentration compared to a standard serum sample calculated as the mean of 3 dilutions in the central segment of the dilution curve.

EXAMPLE 2

Generation of Monoclonal Antibody to Human 1-Antitrypsin

Male Balb/c mice weighing 14–16 g were immunized intraperitoneally (I.P.) with 100 $\mu$g of human $\alpha_1$AT (Sigma Chemical Co.) in complete Freund's adjuvant. The mice were boosted twice by I.P. injection of the $\alpha_1$AT, in incomplete Freund's adjuvant at two weeks and in phosphate buffered saline (PBS) at four weeks. Three days later, the mice were sacrificed and spleens prepared for fusion by the method of St. Groth and Scheidegger (Fazekas de St. Groth S. Scheidegger D. J., 1980, *J. Immunol. Meth.* 35. 1). Single cell suspensions of splenocytes were prepared, and the red blood cells lysed by incubation for two minutes at 0° C. in 0.16M ammonium chloride 0.017M Tris buffer (pH 7.2). After lysis, the splenocytes were centrifuged, resuspended in serum-free Dulbecco s modified Eagle's medium (DMEM). and counted. One hundred million splenocytes were mixed with $10^7$ P3x63Ag8.653 plasmacytoma cells (obtained from Dr. J. Kearney. University of Alabama Medical Center: also available from deposit no. HB 9199). Fusion was performed by gently adding 1 ml of warm (37° C.) 50% PEG 4000 in PBS over a one minute period to the splenocyte-myeloma pellet with continuous mixing. After PEG addition. 5 ml of DMEM was added to the mixture over a five minute period. After the further addition of 5 mls of DMEM, the cells were centrifuged and then gently resuspended in 40 mls of DMEM, 10% FCS HAT (fetal calf serum with hypoxanthine, aminopterin and thymidine) medium and dispensed into 96 well culture dishes containing $3 \times 10^3$ mouse peritoneal macrophages per well. One week after fusion, hybridoma clones were visible. When clones covered 20% of an individual well, a portion of the supernatant was removed for ELISA testing (see below). After positive hybridoma clones were identified, they were expanded into 24-well culture plates containing DMEM, 10% FCS HT (fetal calf serum with hypoxanthine thymidine) medium. Cells were subcloned by diluting to 10 cells/ml and dispensing one drop into each well of 96-well culture dishes containing $3 \times 10^3$ mouse peritoneal macrophages per well. Subclones were retested in the ELISA and progressively expanded by culture in 24 well plates with macrophages. 25 cm² flasks without macrophages and finally 75 cm² flasks without macrophages. After successful propagation 107 cells were suspended in 1 ml of freezing medium (90% FCS. 10% dimethylsulfoxide (DMSO)). frozen overnight at −70° C. and stored in liquid nitrogen.

EXAMPLE 3

ELISA for Screening Hybridomas (1) Direct ELISA for Detecting Antibody to $\alpha_1$AT Dynatech 96 well flat bottom polystyrene microtiter plates were filled with 200 μl of purified human $\alpha_1$AT (Sigma Chemical Co.) diluted to 100 μg/ml in carbonate buffer pH 9.5. The plates were incubated overnight at 4° C. in a humid chamber. Plates were then washed three times with phosphate-buffered saline, pH 7.4 containing 0.05% TWEEN 20 (PBS-TWEEN). Two hundred microliters of culture supernatants diluted 1:3 and 1:10 in PBS-TWEEN were added. Two hundred microliters of mouse polyclonal anti-human $\alpha_1$AT (serum from mice immunized for hybridoma production— these were the same mice that were sacrificed for spleen cells; the mice were bled for serum before being sacrificed for spleen cells.) diluted 1:1000 in PBS-TWEEN was also added to parallel wells as a positive control. Plates were incubated overnight at 37° C. in a humid chamber. Plates were washed three times with PBS-TWEEN and 200 μl per well of affinity-purified peroxidase-labelled goat anti-mouse IgG (Pel-Freez) diluted 1:500 in PBS-TWEEN was added for 2 hours at room temperature. Plates were washed three times with PBS-TWEEN and 200 μl per well of ABTS (Sigma Chemical) in phosphate buffer plus 3 μl/10 ml of 30% hydrogen peroxide was added. Colorimetric results were determined after 20 minutes by using a Dynatech ELISA plate reader.

Using this procedure. 5 clones were identified as reacting in the screening ELISA. One of these was lost during subcloning. The other 4 were tested for specificity in the modified double antibody sandwich ELISA described in Example 1. Of these 4. only 1 showed strong specificity for alpha-1-antitrypsin. This monoclonal antibody, from the hybridoma clone designated LHAT-1 was tested for cross reactivity to albumin, using a modified double antibody sandwich ELISA for albumin described below. Using this assay, the monoclonal antibody to human $\alpha_1$AT available from Cappel Laboratories was compared with the monoclonal antibody produced by clone LHAT-1. The monoclonal antibody produced by clone LHAT-1 was found to react with $\alpha_1$AT significantly more strongly than the Cappel antibody as shown in Table VIII below. In addition, the Cappel antibody was found to cross react strongly with human albumin, while the antibody from LHAT-1 showed no cross reactivity as shown in Table IX below. The monoclonal antibody of the present invention is thus markedly superior to the Cappel antibody.

TABLE VIII

Comparison of Monoclonal Antibody from LHAT-1 with the Cappel Antibody in the Modified Double Antibody Sandwich ELISA for $\alpha_1$AT

| Titer | LHAT-1 | Cappel |
|---|---|---|
| 1:100 | .863 (O.D.) | .803 (O.D.) |
| 1:500 | .840 | .388 |
| 1:1,000 | .757 | .224 |
| 1:2,000 | .609 | .167 |

TABLE IX

Comparison of Monoclonal Antibody from LHAT-1 with the Cappel Antibody in the Modified Double Antibody Sandwich ELISA for Albumin

| Titer | LHAT-1 | Cappel |
|---|---|---|
| 1:100 | .036 (O.D.) | 1.022 (O.D). |

Note: higher numbers indicate stronger reactions. Data represent the average of several replications.

(2) Modified Double Antibody Sandwich ELISA for Detecting Albumin (a) Albumin ELISA Supplies and Reagents The ELISA was performed in 96-well disposable flat-bottomed polyvinyl chloride plates (Dynatech, Alexandria, Va.). Goat polyclonal anti-human albumin was obtained from Cooper Biomedical (Malvern, Pa.). Rabbit anti-human albumin and affinity-purified goat anti-rabbit IgG-peroxidase conjugate were both obtained from Boehringer Mannheim (Indianapolis, Ind). Both antibodies to albumin were prepared from highly purified antigens, were adsorbed to remove nonspecific antibodies and were shown to be monospecific by immunoelectrophoresis against human plasma. ABTS (2,2'-azino-di-(3-ethylbenzthiaoline sulfonic acid)) was obtained from Sigma Chemical Co. A solution of 1 mg/ml ABTS in 0.2M phosphate buffer (pH 7.6) plus 0.003% $H_2O_2$ was used as the substrate. Carbonate/bicarbonate buffer (pH 9.6) was used as the binding buffer for the coating antibody. All other reagent dilutions and washes were made with phosphate-buffered saline (pH 7.45) with 0.05% Tween 20 (PBS-TWEEN).

(b) Albumin Assay

A standard serum sample with an albumin concentration of 45.93 mg/ml was diluted and run as a standard curve for each assay in a range of dilutions from 3 to 1000 ng/ml. The reagents and samples were added sequentially to the microplate wells as described below. After each incubation, the wells were rinsed 3 times with PBS-TWEEN. In the initial step, goat polyclonal anti-human albumin was diluted in carbonate/bicarbonate buffer at a concentration of 10 μg/ml and 100 μl of antibody was added to each well followed by overnight (about 18 hours) incubation at 4° C. in a humidified chamber. Samples and standards were diluted in PBS-TWEEN according to their likely concentration. 100 μl of diluted sample was added to each antibody-coated well followed by a 1 h incubation at 37° C. Rabbit anti-human albumin was diluted 1:1000 in PBS-TWEEN and 100 μl was added to the wells followed by incubation at 37° C. for 2 h in a humidified chamber.

Peroxidase-conjugated: goat anti-rabbit IgG was diluted 1:250 in PBS-TWEEN and 100 μl added to each well. After 1 h incubation at room temperature, 100 μl of substrate solution (1 mg/ml ABTS and 0.003% $H_2O_2$) was added for 10 minutes at room temperature. The optical densities were read at 410 nm using an MS 320 Dynatech microplate reader. Background optical density measured in the absence of albumin was less than 1.0% of the maximum optical density.

The concentration of albumin was determined for multiple 2-fold dilutions of each sample by comparison to a standard curve plotted on log/log paper. The dilutions were chosen to encompass the steep linear portion of the curve as plotted on semilog paper. The original concentration of the sample was calculated by multiplying the albumin concentration of the diluted sample by the dilution factor.

EXAMPLE 4

Double Antibody Sandwich ELISA Using Monoclonal Antibody to Alpha-1-antitrypsin

(1) Biological Samples

The sera used were prepared by allowing blood obtained by venipuncture to clot at room temperature in a glass tube. The sera were aliquoted and frozen at $-70°$ C. until assayed and were subjected to only one freeze-thaw cycle. The $\alpha_1$AT phenotype of each serum was determined by isoelectric focusing as described (Allen, R. C. R. A. Harley and R. C. Talamo, 1974, *Am. J. Clin. Pathol.* 62, 732) using an LKB Multiphor system (produced by LKB Inc., Rockville. Md.) and ultrathin layer electrofocusing gels (pH 4–5) obtained from Accurate Chemical Company (Westbury, N.Y.).

(2) ELISA Supplies and Reagents

The ELISA was performed in 96-well disposable flat-bottomed polyvinyl chloride plates (Dynatech, Alexandria, Va.). Goat polyclonal anti-human $\alpha_1$AT was obtained from Cooper Biomedial (Malvern, Pa.). Supernatant from hybridoma clone LHAT-1 was the source of the mouse anti-human $\alpha_1$AT monoclonal antibody. Affinity purified peroxidase conjugated goat anti-mouse immunoglobulin was obtained from Pel-Freez Biologicals. Salt-free chromatographically prepared human $\alpha_1$AT was obtained from Sigma Chemical Co. (St. Louis, MO) and ABTS (2,2'-azino-di-(3-ethyl-benzthiazoline sulfonic acid)) was obtained from Sigma Chemical Co. A solution of 1 mg/ml ABTS in 0.2M phosphate buffer (pH 7.6) plus 0.003% $H_2O_2$ was used as the substrate. Carbonate/bicarbonate buffer (pH 9.6) was used as the binding buffer for the coating antibody. All other reagent dilutions and washes were made with phosphate-buffered saline (pH 7.45) with 0.05% TWEEN 20 (PBS-TWEEN).

(3) Modified Double Antibody Sandwich ELISA

A standard serum sample (phenotype MM) with an $\alpha_1$AT concentration of 2.45 mg/ml was diluted and run as a standard curve for each assay in a range of dilutions of from 3 to 1000 ng/ml. The reagents and samples were added sequentially to the microplate wells as described below. After each incubation, the wells were rinsed 3 times with PBS-TWEEN. In the initial step, goat polyclonal anti-human $\alpha_1$AT was diluted in carbonate/bicarbonate buffer at a concentration of 25 $\mu$g/ml and 100 $\mu$l of antibody was added to each well followed by overnight incubation at 4° C. in a humidified chamber. Samples and standards were diluted in PBS-TWEEN according to their presumed concentration. 100 $\mu$l of diluted sample was added to each antibody coated well followed by a 2 h incubation at 37° C. Mouse anti-human $\alpha_1$AT from hybridoma clone LHAT-1 was diluted 1:1000 in PBS-TWEEN and 100 $\mu$l was added to the wells followed by incubation at 37° C. for 2 h in a humidified chamber.

Commercially available peroxidase-conjugated goat anti-mouse IgG (obtained from Pel-Freez Biologicals) was diluted 1:250 in PBS-TWEEN and 100 $\mu$l added to each well. After 2 h incubation at room temperature. 100 $\mu$l of substrate solution (1 mg/ml ABTS and 0.003% $H_2O_2$) was added for 30 min at room temperature. The optical densities were read at 410 nm using an MS 320 Dynatech microplate reader. Background optical density measured in the absence of $\alpha_1$AT was less than 1.0% of the maximum optical density.

Figure 3:
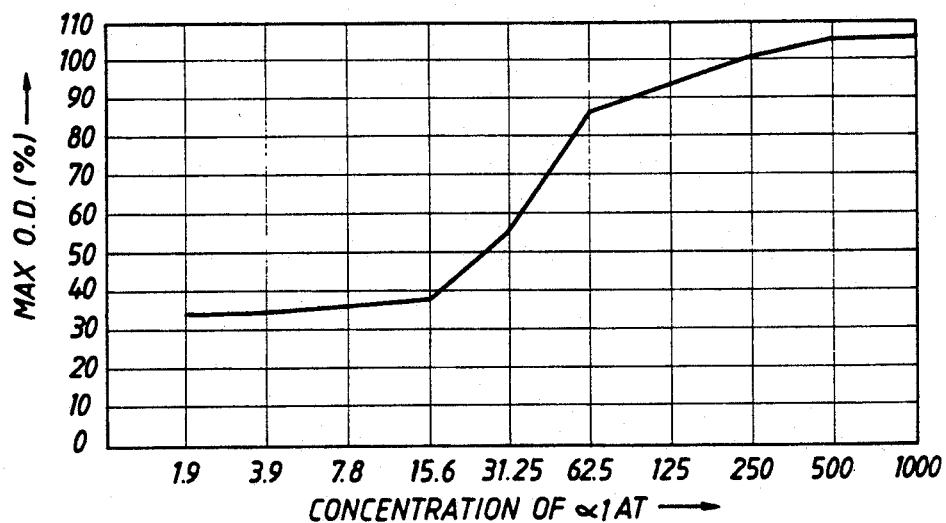
FIG. 3 is a standard curve for alpha-1-antitrypsin measured by an ELISA of this invention using a monoclonal antibody of this invention from hybridoma LHAT-1 of this invention. Abscissa: 2-fold dilutions of serum expressed as ng/ml of $\alpha_1$AT; ordinate: optical density at 410 nm.

The concentration of $\alpha_1$AT was determined for multiple 2-fold dilutions of each sample by comparison to a standard curve. The dilutions were chosen to encompass the steep linear portion of the curve as plotted on semilog paper (FIG. 3). The original concentration of the sample was calculated by multiplying the $\alpha_1$AT concentration of the diluted sample by the dilution factor.

The data is shown in FIG. 3 and Tables VIII and IX above.

While the invention has been described in detail and with reference to specific embodiments thereof, it will be apparent to one skilled in the art that various changes and modifications can be made therein without departing from the spirit and scope thereof.

What is claimed is:

1. A hybridoma cell line having American Type Culture Collection accession number HB-9199, which cell line produces a monoclonal antibody having specific reactivity to $\alpha_1$AT.

2. A composition comprising the hybridoma cell line of claim 1 in a culture medium.

3. A monoclonal antibody having specific reactivity to $\alpha_1$AT, wherein said antibody is produced by a hybridoma cell line having American Type Culture Collection accession number HB-9199.

4. An immunoassay for detecting $\alpha_1$AT in a test sample, comprising the steps of:
reacting a test sample suspected of containing $\alpha_1$AT with the monoclonal antibody of claim 3 to form an antibody-$\alpha_1$AT complex; and
detecting the amount of antibody which reacts with the formed complex.

5. A double antibody immunoassay for detecting alpha-1-antitrypsin ($\alpha_1$AT) in a test sample, comprising the steps of:
immobilizing a first anti-$\alpha_1$AT antibody with a solid substrate;
reacting with the immobilized first antibody in sample suspected of containing $\alpha_1$AT to form a first antibody-$\alpha_1$AT complex;
reacting a labelled second anti-$\alpha_1$AT antibody with the formed complex; and
detecting the amount of labelled second antibody which reacts with the formed complex,
wherein one of said antibodies is the monoclonal antibody of claim 3.

6. The double antibody immunoassay of claim 5 wherein said first antibody is the monoclonal antibody of claim 3.

7. The double antibody immunoassay of claim 5, wherein said second antibody is the monoclonal antibody of claim 3.

8. The immunoassay of claim 4, wherein said test sample comprises biological fluid.

9. The immunoassay of claim 8, wherein said biological fluid is serum.

10. The immunoassay of claim 8, wherein said biological fluid is synovial fluid.

11. The immunoassay of claim 8, wherein said biological fluid is saliva.

12. The immunoassay of claim 8, wherein said biological fluid is bronchoalveolar lavage fluid.

13. An immunoassay kit for detecting $\alpha_1$AT comprising:
   a first antibody specifically reactive with $\alpha_1$AT; and
   a labelled second antibody specifically reactive with $\alpha_1$AT or the first antibody;
   wherein one of said antibodies is the monoclonal antibody of claim 3.

* * * * *